(12) United States Patent
Wall et al.

(10) Patent No.: US 11,439,402 B2
(45) Date of Patent: Sep. 13, 2022

(54) EMBOLIZATION DEVICES AND METHODS OF MANUFACTURING THE SAME

(71) Applicant: Clearstream Technologies Limited, Enniscorthy (IE)

(72) Inventors: Seán Wall, Enniscorthy (IE); Allan Ronan, Enniscorthy (IE)

(73) Assignee: Clearstream Technologies Limited, Enniscorthy (IE)

( * ) Notice: Subject to any disclaimer, the term of this patent is extended or adjusted under 35 U.S.C. 154(b) by 0 days.

(21) Appl. No.: 17/264,441

(22) PCT Filed: Apr. 18, 2019

(86) PCT No.: PCT/EP2019/060106
§ 371 (c)(1),
(2) Date: Jan. 29, 2021

(87) PCT Pub. No.: WO2020/211943
PCT Pub. Date: Oct. 22, 2020

(65) Prior Publication Data
US 2021/0244417 A1      Aug. 12, 2021

(51) Int. Cl.
*A61B 17/12* (2006.01)
*A61B 17/00* (2006.01)

(52) U.S. Cl.
CPC .............. *A61B 17/1215* (2013.01); *A61B 2017/00526* (2013.01)

(58) Field of Classification Search
CPC ........... A61B 2017/00526; A61B 2017/00535; A61B 2017/00561; A61B 2017/00566; A61B 17/1214–12154; A61B 17/12163–12177; A61B 17/12022; A61B 17/12195

See application file for complete search history.

(56) References Cited

U.S. PATENT DOCUMENTS

| 5,573,547 | A |   | 11/1996 | LeVeen et al. |
| 5,623,941 | A |   | 4/1997 | Hedberg et al. |
| 5,911,717 | A | * | 6/1999 | Jacobsen .......... A61B 17/12109 606/1 |

(Continued)

FOREIGN PATENT DOCUMENTS

| CN | 1788638 A | 6/2006 |
| CN | 107249483 A | 10/2017 |

(Continued)

OTHER PUBLICATIONS

International Search Report and Written Opinion pertaining to PCT/EP2019/060106, dated Mar. 27, 2020.

(Continued)

*Primary Examiner* — Katherine H Schwiker
*Assistant Examiner* — Raihan R Khandker
(74) *Attorney, Agent, or Firm* — Dinsmore & Shohl LLP

(57) ABSTRACT

There is provided an embolization device for promoting clot formation in a bodily lumen and having a contracted delivery configuration and an expanded deployed configuration, the embolisation device comprising: a stem comprising a tube having a tube wall; and a plurality of flexible bristles extending radially outwardly from the tube, wherein at least one of the plurality of flexible bristles penetrates through the tube wall.

8 Claims, 18 Drawing Sheets

(56) References Cited

U.S. PATENT DOCUMENTS

| | | | |
|---|---|---|---|
| 5,976,162 A * | 11/1999 | Doan | A61B 17/12022 |
| | | | 606/151 |
| 6,143,007 A | 11/2000 | Mariant et al. | |
| 8,715,314 B1 * | 5/2014 | Janardhan | D04C 3/48 |
| | | | 606/200 |
| 2004/0153120 A1 | 8/2004 | Seifert et al. | |
| 2006/0027244 A1 | 2/2006 | Nomura | |
| 2006/0184194 A1 | 8/2006 | Pal et al. | |
| 2011/0118777 A1 | 5/2011 | Patterson et al. | |
| 2013/0184658 A1 | 7/2013 | Duncan | |
| 2014/0058194 A1 * | 2/2014 | Soletti | B05B 13/0436 |
| | | | 600/36 |
| 2014/0277076 A1 | 9/2014 | Tekulve | |
| 2015/0039017 A1 | 2/2015 | Cragg et al. | |
| 2016/0166257 A1 | 6/2016 | Allen et al. | |

FOREIGN PATENT DOCUMENTS

| | | | |
|---|---|---|---|
| EP | 0739608 | A1 | 4/1996 |
| EP | 0865772 | A1 | 3/1998 |
| EP | 1169969 | A1 | 6/2001 |
| JP | 08336596 | A | 12/1996 |
| JP | 2008500148 | A | 1/2008 |
| JP | 2016509922 | A | 4/2016 |
| JP | 2016511106 | A | 4/2016 |
| WO | 0166190 | A2 | 9/2001 |
| WO | 2005113035 | A2 | 12/2005 |
| WO | 2010067463 | A1 | 6/2010 |
| WO | 2014140325 | A1 | 9/2014 |
| WO | 2014150288 | A2 | 9/2014 |
| WO | 2016041961 | A2 | 3/2016 |

OTHER PUBLICATIONS

Examination Report pertaining to Australian Application No. 2019441553, dated Apr. 9, 2021.

China National Intellectual Property Administration First Search Report dated Jan. 30, 2022 in related Chinese Application for Invention No. 201980059042.3.

Japanese Office Action, Japanese Patent Application No. 2021-503541. dated Apr. 27, 2022.

* cited by examiner

EMBOLIZATION DEVICES AND METHODS OF MANUFACTURING THE SAME

CROSS-REFERENCE TO RELATED APPLICATION

This application is a National Stage Entry, under 35 U.S.C. § 371, of International Patent Application No. PCT/EP2019/060106, filed Apr. 18, 2019, the entirety of which is hereby incorporated by reference.

TECHNICAL FIELD

The present disclosure generally relates to embolization devices for promoting clot formation in a bodily lumen. The present disclosure also generally relates to methods of manufacturing embolization devices for promoting clot formation in a bodily lumen.

BACKGROUND OF THE DISCLOSURE

An embolization device is a permanent or semi-permanent implantable device which may be received within a bodily lumen so as to promote clot formation therein. Such embolization devices may have a contracted delivery configuration and an expanded deployed configuration. The contracted delivery configuration may be such that the device may be loaded into a delivery device, such as a delivery catheter. Various embolization devices are disclosed in WO 2014/140325 and WO 2016/041961, both of which are incorporated herein by reference in their entirety.

Embolization devices may be deployed in the vasculature at a particular location by a medical practitioner so as to promote clot formation and ultimately occlude the blood vessel. However, typical embolization devices may be prone to migration within the vasculature which may cause serious adverse effects.

To reduce migration, some known embolization devices comprise a number of bristles or fibers extending radially outwardly from a central core. The bristles are configured to contact the bodily lumen and anchor the embolization device in the lumen due to friction between the bristles and the wall of the bodily lumen.

However, in these known embolization devices, the bristles may become disconnected from the central core which results in a reduction in the anchoring force and therefore increases the chances of migration of the device.

In addition to bristles, certain embolization devices further include a flow restrictor which acts to restrict flow in the bodily lumen and may further act to provide an additional anchoring force. In these devices, the flow restrictor is typically a separate membrane which is disposed over the central core of the embolization device. During assembly of the device, the flow restrictor must therefore be manipulated such that it is attached to the central core. However, this may result in an unreliable attachment and deformations or irregularities in the attached flow restrictor.

Accordingly, such flow restrictors may not reliably expand to their expanded deployed configuration in the bodily lumen, and, therefore, the additional anchoring force provided by the flow restrictor may not reliably come about when the device is deployed. Again, this increases the chances of migration of the device.

In view of the above, there is a need for an improved embolization device which is capable of achieving and maintaining an anchoring force more reliably. There is also a need for an improved method of manufacturing an embolization device which is capable of achieving and maintaining an anchoring force more reliably.

BRIEF DESCRIPTION OF THE DRAWINGS

For a better understanding of the present disclosure, and to show how the same may be carried into effect, reference will be made, by way of example only, to the following drawings, in which.

DETAILED DESCRIPTION

Figure 1:
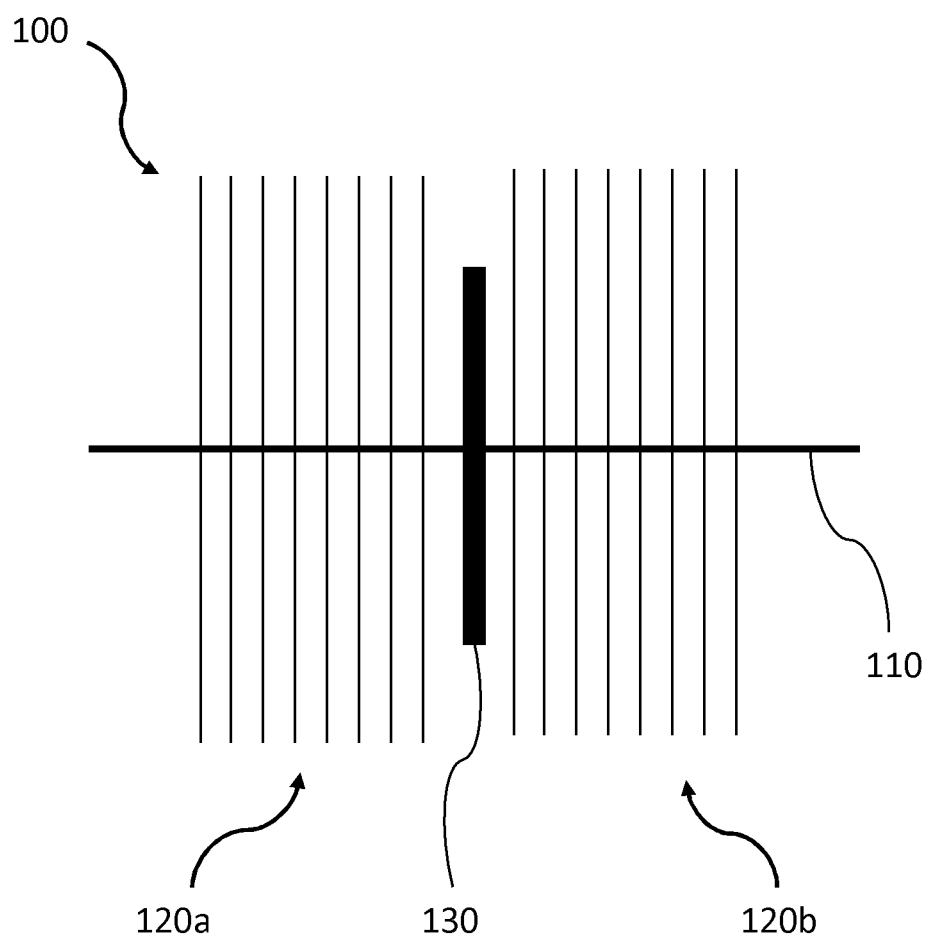
FIG. 1 shows an embolization device in an unconstrained configuration.

There is provided an embolization device for promoting clot formation in a lumen. The embolisation device may have a contracted delivery configuration and an expanded deployed configuration. The embolization device may comprise a stem comprising a tube having a tube wall. The embolization device may comprise a plurality of flexible bristles extending radially outwardly from the tube. At least one of the plurality of flexible bristles may penetrate through the tube wall.

Throughout this disclosure, the term 'embolization device' may refer to a device which may be permanently or semi-permanently implanted in a bodily lumen. Accordingly, the 'embolization device' may be configured to be disposed within the bodily lumen for a period of time, such as a number of days, or disposed in the bodily lumen indefinitely. To this end, the 'embolization device' may be configured to be selectively detached from a delivery element so that it may be implanted in the bodily lumen in isolation.

Throughout this disclosure, a 'contracted delivery configuration' of an element may refer to a configuration of the element which has a smaller radial extent than an 'expanded deployed configuration' of the element.

Throughout this disclosure, the term 'tube wall' may refer to the wall of a tube which extends along the longitudinal axis of the tube. The tube wall may be continuous or discontinuous.

Throughout this disclosure, the term 'tube' may refer to any element which has a tube wall in which different portions of the tube wall oppose each other across a longitudinal axis. For example, the tube wall may be curved (e.g. having a circular cross-section) around the longitudinal axis of the tube such that opposite sides of the tube wall oppose each other. The tube may or may not have a lumen extending along any portion of its longitudinal axis.

The tube wall may have one or more slits extending along part or all of the longitudinal length of the tube.

The tube may be an elongate tube.

The tube may not comprise a coil.

The tube may have a lumen extending along its longitudinal axis. A portion of the at least one of the plurality of flexible bristles that penetrates through the tube wall is disposed in the lumen.

The tube may have two or more lumens extending along its longitudinal axis. At least some of the two or more lumens are substantially isolated from one another. At least some of the two or more lumens are spaced apart along the longitudinal axis of the tube. A portion of the at least one of the plurality of flexible bristles is disposed in one of the two or more lumens.

The tube may have a smaller radial extent in a portion adjacent to at least one of the two or more lumens than the radial extent of the tube at a portion corresponding to the at least one of the two or more lumens. The portion adjacent to at least one of the two or more lumens may be disposed between two portions of the tube corresponding to two lumens.

The portion of the at least one of the plurality of flexible bristles that penetrates through the tube wall substantially fills a lumen of the tube.

Throughout this disclosure, as would be understood by the skilled person, the term 'stem' refers to an elongate element which extends longitudinally along the length of the embolization device to act as a backbone for the device, and has a significantly smaller radial extent than the further elements of the embolization device (for example, the plurality of flexible bristles). The stem may extend along substantially the whole longitudinal extent of the plurality of flexible bristles (e.g. when the embolization device is in an unrestrained configuration, contracted delivery configuration and/or expanded deployed configuration). The stem may extend along substantially the whole length of the embolization device.

In any of the embodiments described herein, as would be understood by the skilled person, the term 'bristle' may refer to an elongate strand of material formed substantially a single piece. The 'bristle' may be a resilient bristle. The resilient bristle may be biased towards a particular curvature.

Throughout this disclosure, the term 'radially outwardly' does not exclude the element additionally extending in the longitudinal direction of the device. For example, the plurality of flexible bristles may extend radially outwardly and longitudinally from the tube.

The plurality of flexible bristles may have a contracted configuration in the contracted delivery configuration. The plurality of flexible bristles may have an expanded configuration in the expanded deployed configuration.

In the expanded configuration, the plurality of flexible bristles may be configured to anchor the device in the bodily lumen. The plurality of flexible bristles may be configured to provide substantially all of the anchoring force for the embolization device in the bodily lumen.

In the expanded configuration, the plurality of flexible bristles may be configured to contact the bodily lumen.

Throughout this disclosure, the term 'penetrates through' refers to an object passing into and through another object.

A portion of the at least one of the plurality of flexible bristles is clamped between two opposing sides of the tube wall.

Throughout this disclosure, an element referred to as being 'clamped between' two clamping elements, refers to the two clamping elements directly or indirectly providing forces (for example, opposing forces) on the element so as to restrain the element. The clamping elements may directly or indirectly contact the clamped element.

The tube may be formed from a shrinkable material. The tube may be formed from a heat shrinkable material. The tube may be formed of a chemically shrinkable material.

Throughout this disclosure, a 'shrinkable material' may refer to a material which shrinks in a particular direction upon a particular treatment. Such a treatment may be a heat and/or or chemical treatment. As would be understood by the skilled person, the shrinkable materials themselves shrink without an external force being applied to them, for example, by crimping.

The tube may be shrunk such that a portion of the at least one of the plurality of flexible bristles is clamped between two opposing sides of the tube wall.

The tube may be shrunk in a radial direction of the tube. Additionally or alternatively, the tube may be shrunk in an axial direction of the tube.

The tube may be mechanically compressed in a radial direction such that a portion of the at least one of the plurality of flexible bristles is clamped between two opposing sides of the tube wall. The tube may be mechanically compressed by crimping.

Throughout this disclosure, the term 'mechanically compressing' an element refers to a compression which is caused by a mechanical interaction between an external device and the element.

The tube may be formed from a meltable or melted material.

At least a portion of the tube or substantially the whole tube may have been melted such that a portion of the at least one of the plurality of flexible bristles is secured to the tube.

At least a portion of the tube or substantially the whole tube may have been melted to allow the melted material of the tube to surround a portion of the flexible bristle(s).

Thereafter, the melted material may have been allowed to solidify such that the portion is secured.

A filler material may be disposed within a lumen of the tube to secure the at least one of the plurality of flexible bristles to the tube.

The filler material may be an adhesive.

The filler material may be a curable material or a settable material. The filler material may be curable or settable upon heating, solvent flashing and/or irradiating.

The filler material may adhere or bond to the at least one of the plurality of flexible bristles. Additionally or alternatively, the filler material may mechanically anchor the at least one of the plurality of flexible bristles.

Throughout this disclosure, the term 'mechanically anchor' refers to the anchoring of an element substantially by mechanical forces caused by the macroscopic properties of the anchoring element, rather than intermolecular forces and/or chemical bonds between the anchoring element and the anchored element which are responsible for adhering/bonding.

The filler material may substantially fill the lumen of the tube.

The embolization device may further comprise a securing piece disposed within a lumen of the tube. The securing piece may be configured to secure the at least one of the plurality of flexible bristles to the tube.

A portion of the at least one of the plurality of flexible bristles may be clamped between the securing piece and an inner surface of the tube wall.

The securing piece may be an inner mandrel.

The securing piece may be an inner mandrel, where a portion of the at least one of the plurality of flexible bristles may be clamped between an outer surface of the inner mandrel and an inner surface of the tube wall.

A portion of the at least one of the plurality of flexible bristles which penetrates through the tube wall may have a greater radius than a hole in the tube wall through which the bristle penetrates the tube wall.

The portion of the at least one of the plurality of flexible bristles that penetrates through the tube wall may be a portion which is disposed within a lumen of the tube.

The portion of the at least one of the plurality of flexible bristles disposed within a lumen of the tube may have a greater radius than a hole in the tube wall through which the bristle penetrates the tube wall.

A portion of the at least one of the plurality of flexible bristles which penetrates through the tube wall may comprise an anchoring section.

A portion of the at least one of the plurality of flexible bristles which penetrates through the tube wall may comprise a rough portion.

The rough portion may be rougher than another portion of the flexible bristle. The another portion may be a portion of the flexible bristle which extends radially outwardly from the tube wall.

The tube wall may have one or more holes defined therein. Each of the one or more holes may be configured to receive one or more of the plurality of flexible bristles.

The tube wall may have one or more pre-machined holes. The pre-machined hole(s) may be configured to receive one or more of the plurality of flexible bristles.

Throughout this disclosure, a 'pre-machined hole' refers to a hole which is created in a piece of material. For example, a pre-machined hole may be a hole which is machined in a continuous wall of the tube. The 'machining' may be carried out in various ways, for example, drilling or lasering.

The hole or pre-machined hole may receive only one of the at least one of the plurality of flexible bristles. The hole or pre-machined hole receives only two, three or four of the at least one of the plurality of flexible bristles.

The hole(s) or pre-machined hole(s) may have substantially the same diameter as the flexible bristle which passes therethrough.

The holes in the tube wall described anywhere herein may be arranged so as to arrange the flexible bristles in a prescribed manner. For example, the holes may be oriented such that the flexible bristles are distributed substantially evenly around the circumference of the stem. Additionally or alternatively, the plurality of holes may be arranged in spaced-apart segments. Optionally, a space between two spaced-apart segments may accommodate a flow restrictor.

The at least one of the plurality of flexible bristles may penetrate through the tube wall at a first location and penetrate through the tube wall at a second location.

The first location is different from the second location.

The first location and the second location may be on substantially opposite sides of the circumference of the tube.

The first location and the second location may be on the same half, third, quarter, fifth or sixth of the circumference of the tube.

The first location and the second location may be substantially axially aligned.

There is provided a method of manufacturing an embolization device for promoting clot formation in a lumen having a contracted delivery configuration and an expanded deployed configuration. The method may comprise providing a stem comprising a tube having a tube wall. The method may comprise providing a plurality of flexible bristles such that they extend radially outwardly from the tube. At least one of the plurality of flexible bristles may penetrate through the tube wall.

The method may comprise clamping the at least one of the plurality of flexible bristles between two opposing sides of the tube wall.

The method may comprise shrinking or mechanically compressing the tube such that a portion of the at least one of the plurality of flexible bristles is clamped between two opposing sides of the tube wall.

The tube may be shrunk or compressed in a radial direction of the tube. Additionally or alternatively, the tube may be shrunk or compressed in an axial direction of the tube.

The method may comprise melting at least a portion of the tube or substantially the whole of the tube such that a portion of the at least one of the plurality of flexible bristles is secured to the tube.

At least a portion of the tube or substantially the whole tube may be melted to allow the melted material of the tube to surround a portion of the flexible bristle(s). Thereafter, the melted material may be allowed to solidify such that the portion is secured.

The method may comprise disposing a filler material within a lumen of the tube to secure the at least one of the plurality of flexible bristles to the tube. The filler material may be disposed within the lumen before or after penetrating the at least one of the plurality of flexible bristles through the tube wall.

The filler material may be an adhesive.

The filler material may be cured or set. The filler material may be cured or set upon heating, solvent flashing and/or irradiating.

The filler material may adhere or bond to the at least one of the plurality of flexible bristles. Additionally or alternatively, the filler material may mechanically anchor the at least one of the plurality of flexible bristles.

The filler material may substantially fill the lumen of the tube.

The method may comprise disposing a securing piece within a lumen of the tube so as to secure the at least one of the plurality of flexible bristles to the tube.

A portion of the at least one of the plurality of flexible bristles may be clamped between the securing piece and an inner surface of the tube wall The securing piece may be an inner mandrel. A portion of the at least one of the plurality of flexible bristles may be clamped between an outer surface of the inner mandrel and an inner surface of the tube wall.

The tube may be shrunk or mechanically compressed. Additionally or alternatively, the securing piece may be radially expanded once the securing piece is disposed within the lumen such that the portion of the at least one of the plurality of flexible bristles is clamped between the securing piece and an inner surface of the tube wall.

The method may comprise machining a hole in the tube wall and receiving one or more of the at least one of the plurality of flexible bristles in the hole.

A portion of the at least one of the plurality of flexible bristles which penetrates through the tube wall has a greater radius than a hole in the tube wall through which the bristle penetrates the tube wall.

The method may comprise penetrating the at least one of the plurality of flexible bristles through the tube wall at a first location and penetrating the flexible bristle through the tube wall at a second location.

The method may comprise inserting a guide into a lumen of the tube such that a portion of the flexible bristle may be guided from the inside of the lumen through a hole to the outside of the tube.

There is provided an embolization device for promoting clot formation in a lumen and having a contracted delivery configuration and an expanded deployed configuration. The embolization device may comprise a stem formed from a material. The embolization device may comprise a plurality of flexible bristles extending radially outwardly from the stem. A portion of at least one of the plurality of flexible bristles may be disposed within a volume of the material of the stem such that the material surrounds and secures the portion of the flexible bristle.

Throughout this disclosure, reference to the 'volume of the material' may refer to a bulk or homogenous volume of the material. The volume of material is formed from a continuous portion of the material rather than two substantially individual elements (such as two opposing individual wires).

A portion of the flexible bristle is disposed within this 'volume of material'. Accordingly, the portion is disposed within a bulk or homogenous volume of the material rather than between two substantially individual elements (for example, a flexible bristle held between two opposing individual wires).

Throughout this disclosure, as would be understood by the skilled person, a 'stem being formed from a material' refers to a stem where a significant portion of the stem's volume along which the bristles are attached is formed of the material. The stem's structural properties may be largely dictated by the material and its form rather than any other components of the stem. Accordingly, the stem may be formed substantially of the material.

The material need not be uniform. The material may have different properties and/or compositions in different portions of the stem. For example, the composition of the stem may change gradually from one part of the stem to another.

The material may adhere or bond to the portion of the at least one of the plurality of flexible bristles.

The material may mechanically anchor the portion of the at least one of the plurality of flexible bristles.

The material may be a curable material or settable material. The material may be curable or settable upon heating, solvent flashing and/or irradiating.

The material may be cured or set such that the material surrounds and secures the portion of the flexible bristle.

As used throughout herein, the 'material' may refer to the 'filler material' which is described herein.

The portion may comprise a rough portion.

The rough portion may be rougher than some or all other portions of the flexible bristle, and, in particular, the free portion which extends radially outwardly.

The portion may comprise a thick portion or anchoring portion.

The thick portion may be thicker than some or all other portions of the flexible bristle, and, in particular, the free portion which extends radially outwardly.

The stem may further comprise a covering element disposed on at least a portion of an outer surface of the material.

The covering element may be a tube. The material may be disposed within the tube.

The covering element may be in the form of a sheet. The sheet may be a curved sheet.

The stem may further comprise an inner element. The inner element may be disposed at last partially within the material. The inner element may extend along at least a portion of the length of the material.

The inner element may be elongated. The inner element may be rod-shaped.

The embolization device may further comprise a flow restrictor integral to the material of the stem. The flow restrictor may be formed from the material.

The flow restrictor may be a flow restricting membrane.

Any of the 'flow restrictors' or 'flow restricting membranes' disclosed herein may have a contracted configuration in the contracted delivery configuration. Any of the 'flow restrictors' or 'flow restricting membranes' disclosed herein may have an expanded configuration in the expanded deployed configuration.

In the expanded configuration, any of the 'flow restrictors' or 'flow restricting membranes' disclosed herein may be configured to anchor the device in the bodily lumen. The 'flow restrictor' or 'flow restricting membrane' may be configured to provide substantially all of the anchoring force for the embolization device in the bodily lumen.

In the expanded configuration, any of the 'flow restrictors' or 'flow restricting membranes' disclosed herein may be configured to contact the bodily lumen.

The material may be a polymer. The material may be a nylon. The material may be a resin. The material may be a metal and/or an alloy.

The portion of the at least one of the plurality of flexible bristles disposed within the material of the stem may extend substantially in a radially outward direction.

The portion of the at least one of the plurality of flexible bristles disposed within the material of the stem may extend substantially transversely to the longitudinal axis of the stem.

The at least one of the plurality of flexible bristles may substantially perpendicularly intersect the stem, preferably, at least in the unconstrained configuration of the embolisation device.

There is provided a method of manufacturing an embolization device for promoting clot formation in a lumen and having a contracted delivery configuration and an expanded deployed configuration. The method may comprise providing a stem formed from a material. The method may comprise providing a plurality of flexible bristles extending radially outwardly from the stem. A portion of at least one of the plurality of flexible bristles may be disposed within a volume of the material of the stem such that the material surrounds and secures the portion of the flexible bristle.

The method may comprise adhering or bonding the material to the portion of the at least one of the plurality of flexible bristles.

The method may comprise mechanically anchoring the portion of the at least one of the plurality of flexible bristles to the material.

The method may comprise curing or setting the material such that it surrounds and secures the portion of the flexible bristle. The curing or setting may be upon heating, solvent flashing and/or irradiating.

The method may comprise molding the material in a mold.

The method may comprise disposing the portion of the flexible bristle inside the mold such that the flexible bristle penetrates through a wall of the mold.

The step of disposing the portion of the flexible bristle inside the mold may occur before or after molding the material in a mold.

At least a portion of the mold may be a tube having a tube wall.

The tube may not be removed such that it forms a part of the final embolization device.

The embolization device may comprise the tube forming at least part of the mold.

The method may comprise shaping the material into the stem.

The method may comprise inserting the portion into the shaped stem. The method may comprise curing or setting the material.

The method may further comprise providing an inner element disposed at last partially within the material.

The inner element may be disposed within the material before the material is cured or set.

The inner element may be disposed within the material after the material is cured or set. The inner element may be inserted into a hole within the material. The hole may be created by the inner element itself and/or another device, such as a drill.

There is provided an embolization device for promoting clot formation in a lumen and having a contracted delivery configuration and an expanded deployed configuration. The embolization device may comprise a stem formed from a material. The embolization device may comprise a plurality of flexible bristles extending radially outwardly from the stem. The embolization device may comprise a flow restrictor extending radially outwardly from the stem. The flow restrictor may be formed from the material. The flow restrictor may be integrally formed with the material of the stem.

Throughout this disclosure, as would be understood by the skilled person, an element referred to as being 'integrally formed with the material' of another element means that the two elements are formed in such a way that there is no distinct, identifiable connection between the two elements. The two elements may be formed form the same material. The two elements may be considered as one and the same.

The material may be a curable material or settable material. The material may be a curable material or settable material which is curable or settable upon heating, solvent flashing and/or irradiating.

The material may be a moldable material.

The material may be molded to integrally form the flow restrictor and the stem.

At least a portion of at least one of the plurality of flexible bristles may be disposed within a volume of the material of the flow restrictor and/or stem.

The at least a portion may be disposed within the volume of the material of the flow restrictor and/or stem such that the material surrounds and secures the portion of the flexible bristle.

The entirety of the at least one of the plurality of flexible bristles may be disposed within a volume of the material of the flow restrictor and/or stem.

The flow restrictor may be resilient and/or pre-curved.

The flow restrictor may be a flow restricting membrane.

The flow restrictor may comprise two or more individual segments.

The two or more individual segments may not be directly connected. Each of the two or more individual segments may be directly connected to the stem.

The stem may further comprise a covering element disposed on at least a portion of an outer surface of the material of the stem. The covering element may be a tube. The material may be disposed within the tube.

The covering element may be in the form of a sheet. The covering element may be a curved sheet.

The flow restrictor may further comprise a covering element disposed on at least a portion of an outer surface of the material of the flow restrictor.

The covering element may comprise two membranes. The material may be disposed between the two membranes. Each of the two membranes may extend radially outwardly from the stem.

The covering element may additionally or alternatively cover at least partially a surface of the material of the flow restrictor which extends substantially longitudinally.

There is provided a method of manufacturing an embolization device for promoting clot formation in a lumen and having a contracted delivery configuration and an expanded deployed configuration. The method may comprise providing a stem formed from a material. The method may comprise providing a plurality of flexible bristles extending radially outwardly from the stem. The method may comprise providing a flow restrictor extending radially outwardly from the stem. The flow restrictor may be formed from the material. The flow restrictor may be integrally formed with the material of the stem.

The stem and the flow restrictor may be molded in a mold. The mold may be a single mold. The mold may define a single, continuous mold cavity.

The method may comprise disposing a portion of at least one of the flexible bristle inside the mold such that the at least one of the flexible bristles penetrates through a wall of the mold.

At least a portion of the mold may be a tube having a tube wall.

The embolization device may comprise the tube.

The tube may not be removed such that it forms a part of the final embolization device.

The embolization device may comprise the tube forming at least part of the mold.

A portion of the mold cavity defining the flow restrictor may be curved.

The method may comprise shaping the material into the stem and the flow restrictor.

Throughout this disclosure, the exemplary materials disclosed in relation to the 'filler material' are also exemplary materials for the 'material' referred to herein, and vice versa.

In any of the embodiments disclosed herein in which a flexible bristle penetrates through the tube wall, the tube wall may surround substantially the entire cross-sectional perimeter of the flexible bristle.

In any of the embodiments disclosed herein, the filler material may comprise or consist of: medical grade 2 part epoxy resin, polyurethane, nylon 12, Pebax 4033, liquid crystal polymer, polyether ether ketone, polycarbonate, neoprene, acrylate polymers or any combination thereof.

In any of the embodiments disclosed herein, the heat shrinkable material may comprise or consist of: polyolefin, Pebax, FEP, PTFE, PFA, ETFE, PET, polyether ether ketone or any combination thereof.

FIG. 1 shows an embolization device 100. The embolization device 100 is configured for deployment in a bodily lumen so as to promote clot formation therein. The embolization device 100 in FIG. 1 is shown in an unconstrained configuration.

The embolization device 100 comprises a stem 110, a plurality of flexible bristles 120a, 120b and a flow restricting membrane 130. In any of the embodiments described herein, the flow restricting membrane 130 is optional.

The stem 110 extends along the longitudinal length of the embolization device 100. The stem 110 may extend along substantially the whole longitudinal length of the embolization device 100 when the embolization device 100 is in the unconstrained configuration.

The stem 110 may be flexible, for example, flexible along substantially its entire length. The stem 110 may be flexible such that the embolization device 100 when deployed in a bodily lumen conforms to the shape of the bodily lumen. The stem 110 may have flexible sections, hinges and/or connectors (not shown) disposed along its length. Additionally or alternatively, the stem 110 may have a pre-curved shape.

A portion of the stem 110, for example, a proximal portion, may have a detachment mechanism (not shown) configured to be removably attachable to a delivery element, such as a delivery wire. For example, the detachment mechanism may be female screw hole.

FIG. 1 shows the plurality of flexible bristles 120a, 120b as two spaced-apart segments of bristles in the form of a proximal bristle segment 120a and a distal bristle segment 120b which are spaced apart along the longitudinal length of the stem 110. However, as would be understood by the skilled person, various arrangements of the plurality of flexible bristles 120a, 120b is possible, for example, in any number of segments, including a single segment. Furthermore, the plurality of flexible bristles 120a, 120b need not be identical and may have, for example, different lengths, materials, flexibilities and/or thicknesses.

Each of the plurality of flexible bristles 120a, 120b is secured to the stem 110 and extends radially outwardly from the stem 110.

Each of the plurality of flexible bristles 120a, 120b may be spaced apart along the longitudinal length of the stem 110.

In certain embodiments, at least some of the plurality of flexible bristles 120a, 120b may be disposed at the same axial location along the stem 110.

The flow restricting membrane 130 may be attached to the stem 110. The flow restricting membrane 130 may have a hole therein through which the stem 110 passes, however, other arrangements are contemplated herein.

The flow restricting membrane 130 may extend radially outwardly from the stem 110. The flow restricting membrane 130 may be of any shape, for example, generally circular. The flow restricting membrane 130 may be flexible, resilient and/or pre-curved. In alternative embodiments, the flow restricting membrane 130 may be any kind of flow restrictor.

The flow restricting membrane 130 may be disposed between some of the plurality of flexible bristles 120a, 120b. In certain embodiments, the flow restricting membrane 130 may be disposed between the proximal bristle segment 120a and the distal bristle segment 120b, as shown in FIG. 1.

Figure 2:
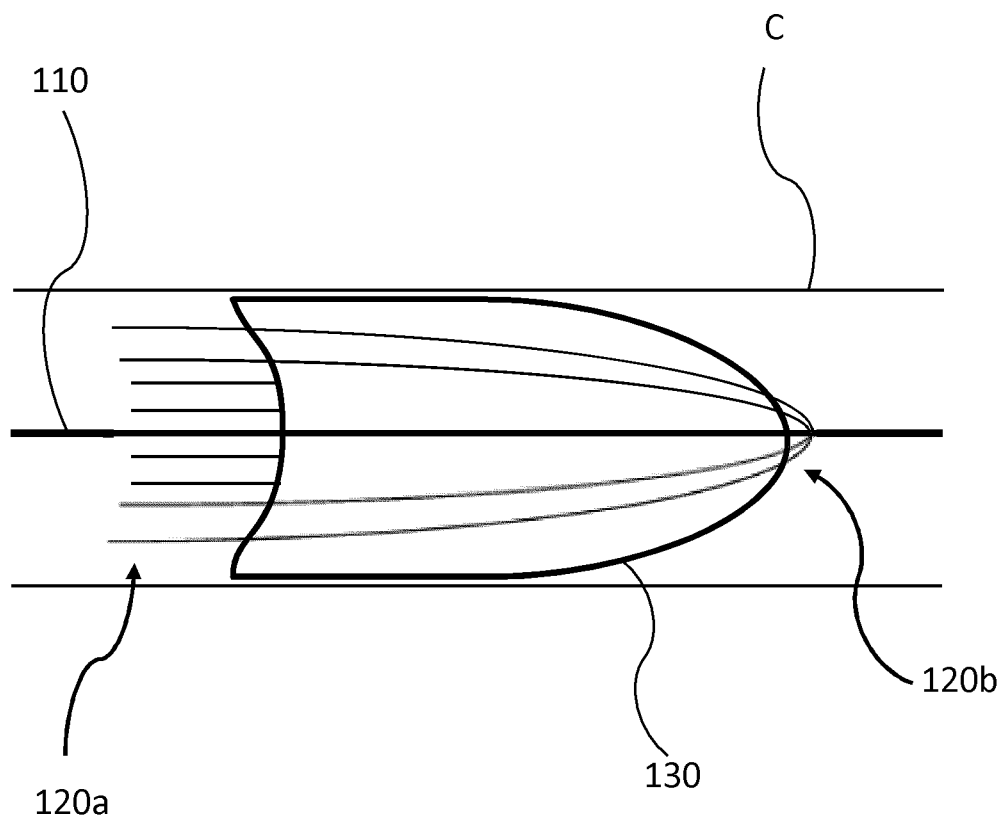
FIG. 2 shows the embolization device of FIG. 1 in a contracted delivery configuration within a delivery catheter.

FIG. 2 shows the embolization device 100 in a contracted delivery configuration within a delivery catheter C.

As can be seen from FIG. 2, in the contracted delivery configuration of the embolization device 100, the plurality of flexible bristles 120a, 120b have been collapsed into a contracted configuration.

As also can be seen from FIG. 2, in the contracted delivery configuration of the embolization device 100, the flow restricting membrane 130 has been collapsed into a contracted configuration.

In FIG. 2, both the proximal bristle segment 120a and the distal bristle segment 120b point proximally. However, as will be evident to the person skilled in the art, any arrangement in this regard is possible. In particular, the proximal bristle segment 120a and the distal bristle segment 120b may point distally. The proximal bristle segment 120a may point proximally and the distal bristle segment 120b may point distally. The proximal bristle segment 120a may point distally and the distal bristle segment 120b may point proximally.

Figure 3:
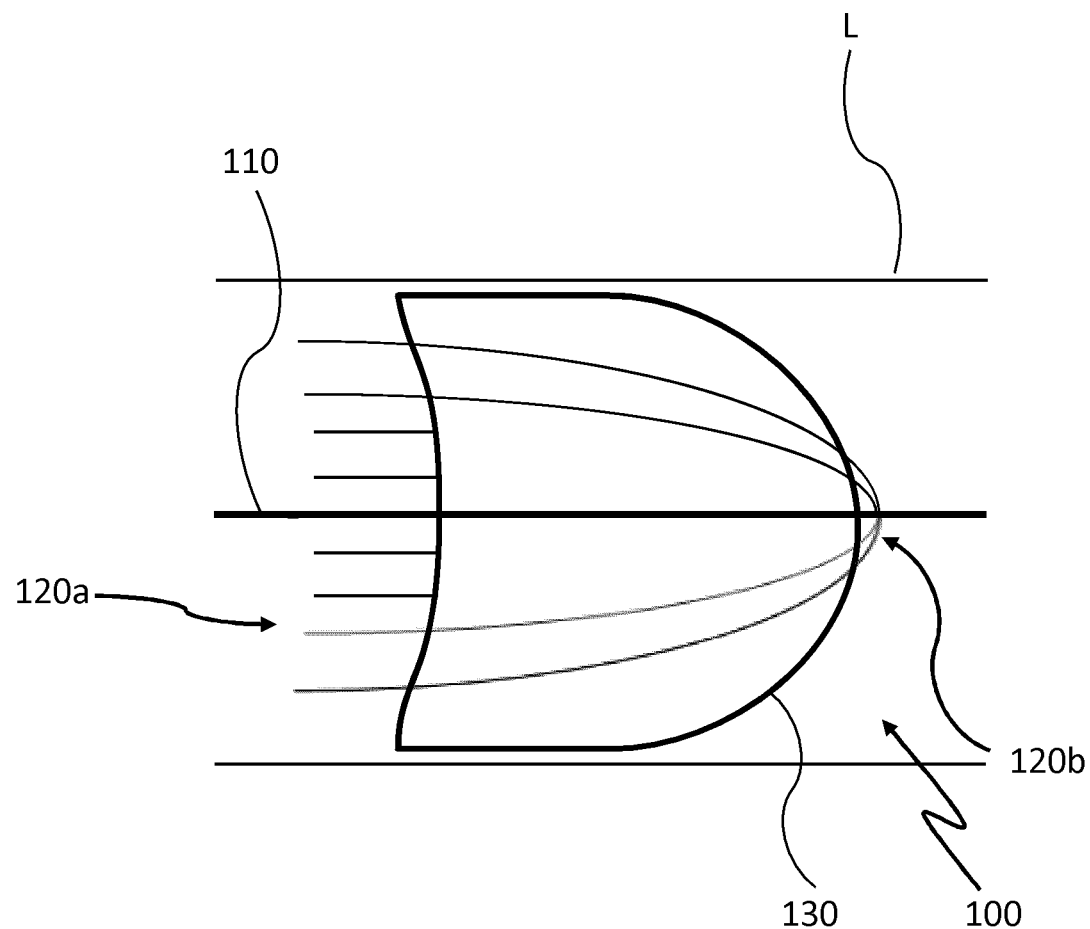
FIG. 3 shows the embolization device of FIGS. 1 and 2 in an expanded deployed configuration in a bodily lumen.

FIG. 3 shows the embolization device 100 in an expanded deployed configuration in a bodily lumen L. The embolization device 100 may be disposed within the bodily lumen L in the expanded deployed configuration by removing the delivery catheter C whilst inserted in the bodily lumen L such that the embolization device 100 is allowed to expand in the bodily lumen L.

The expanded deployed configuration of the embolization device 100 has a greater radial extent than the contracted delivery configuration shown in FIG. 2. In the expanded deployed configuration shown in FIG. 3, the plurality of flexible bristles 120a, 120b and the flow restricting membrane 130 contact the bodily lumen L so as to anchor the embolization device 100 within the bodily lumen L. The anchoring force provided by the plurality of flexible bristles 120a, 120b and the flow restricting membrane 130 may be sufficient to resist migration of the embolization device 100 in the bodily lumen L.

In the expanded deployed configuration shown in FIG. 3, the embolization device 100 may occlude the bodily lumen L and promote clot formation therein.

FIGS. 1 to 3 show a purely exemplary particular form of embolization device, however, aspects of the present disclosure need not be applied specifically to the form of embolization described in reference to these figures. Accordingly, various modifications may be made to the overall structure/arrangement of the described embolization device, such as a different number/arrangement of bristle segments, number of bristles in each bristle segment, types of bristles within each bristle segment. Furthermore, connections/hinges may be present along the length of the stem, for example, between some or all of the bristle segments.

In this regard, reference is made to the embolization devices disclosed in each of WO 2014/140325 and WO 2016/041961, both of which are incorporated herein by reference in their entirety.

Figure 4:
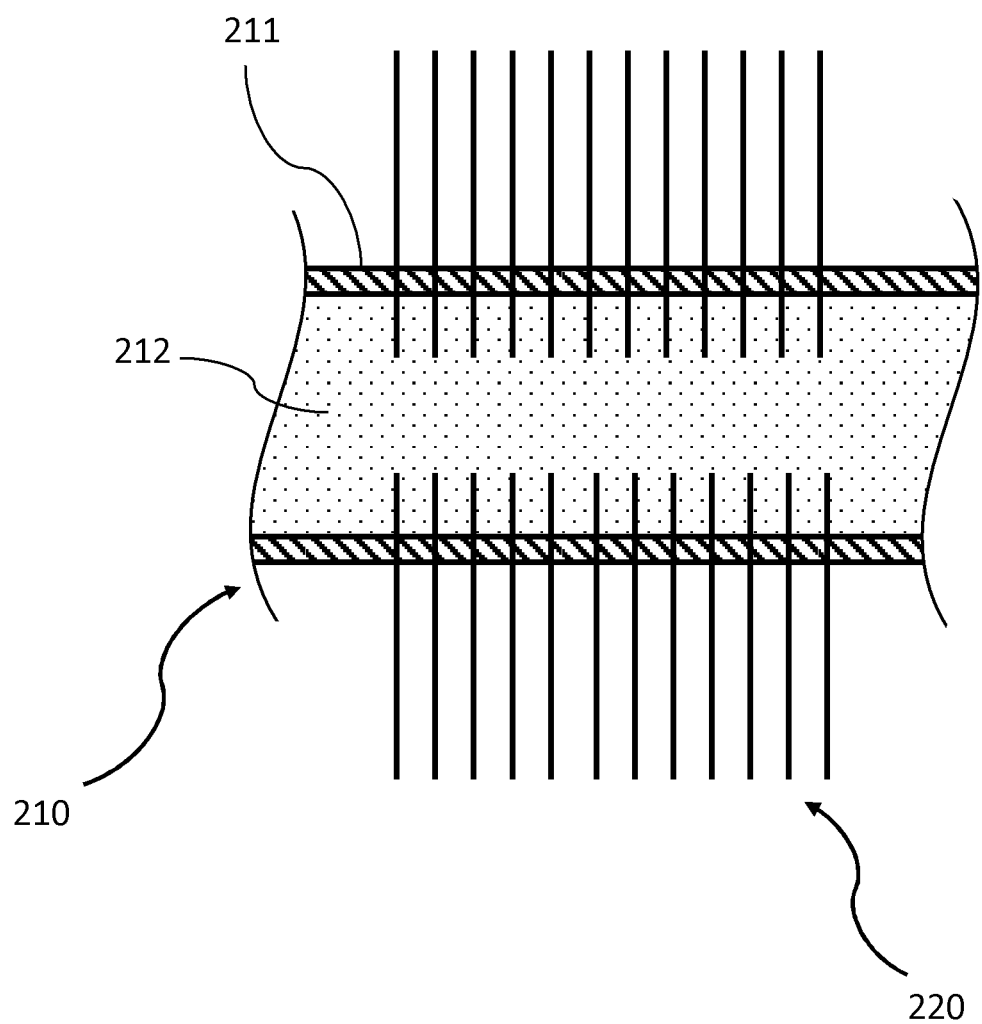
FIGS. 4 to 8 each show a cross-section along part of the length of various embodiments of the embolization device.

FIG. 4 shows a cross-section along part of the length of an embodiment of the embolization device, and, in particular, the stem 210 and flexible bristles 220.

The stem 210 comprises a tube having a tube wall 211. The tube may be generally cylindrical. The tube may define a lumen along the longitudinal axis of the tube.

The plurality of flexible bristles 220 extend radially outwardly from the tube, and, in particular, the tube wall 211. The plurality of flexible bristles 220 each penetrate through the tube wall 211.

As shown in FIG. 4, the plurality of flexible bristles 220 each penetrate through the tube wall 211 such that a portion of each of the flexible bristles 220 is disposed within the lumen of the tube.

The tube wall 211 may have a plurality of holes therein (not shown) through which, for example, a single one or some of the plurality of flexible bristles 220 passes therethrough. The holes may each have substantially the same diameter as the flexible bristle which passes therethrough.

The plurality of holes in the tube wall 211 may be arranged so as to arrange the flexible bristles 220 in a prescribed manner. For example, the plurality of holes may be oriented such that the flexible bristles 220 are distributed substantially evenly around the circumference of the stem 210. Additionally or alternatively, the plurality of holes may be arranged in spaced-apart segments. Optionally, a space between two spaced-apart segments may accommodate a flow restricting membrane.

The stem 210 further comprises filler material 212 disposed within the lumen of the tube. As shown in FIG. 4, the filler material 212 may substantially fill the lumen of the tube.

The filler material 212 disposed within the lumen of the tube may engage the portions of the flexible bristles 220 which are disposed within the lumen of the tube. The filler material 212 may act to secure the plurality of flexible bristles 220 to the stem 210.

The filler material 212 may be an adhesive. In such embodiments, the filler material 212 may engage the flexible bristles 210 by adhering or bonding to the flexible bristles 210.

The filler material may be a curable material or settable material, which is curable or settable upon heating, solvent flashing and/or irradiating. Upon curing or setting, the material may harden so as to secure the flexible bristles 220 to the stem 210.

The filler material 212 may engage the flexible bristles 220 by mechanically anchoring the flexible bristles 220 to the stem 210.

As one (or a sub-set) of the plurality of flexible bristles 220 passes through each hole in the tube wall 211, the flexible bristles 220 are attached to the stem individually or in a (small) sub-set. Accordingly, if the integrity of the attachment of one of the flexible bristles becomes compromised, the integrity of the attachments of the other flexible bristles may not be compromised. For example, if one of the plurality of flexible bristles 220 is dislodged from the stem 210, the attachment of the remaining flexible bristles may remain uncompromised, which is not the case when the majority of the attachment force for a particular bristle is provided for by surrounding/neighbouring bristles.

The stem 210 and flexible bristles 220 of the embolization device may be manufactured by creating, for example, by machining, a plurality of holes in the tube wall 211 of the tube. One of the plurality of flexible bristles 220 may be inserted through each of the plurality of holes in the tube wall 211 such that a portion of each of the flexible bristles 220 extends into the lumen of the tube and a free portion of each of the flexible bristles 220 extends radially outwardly from the tube wall 211.

The filler material 212 may be disposed in the lumen of the tube. The filler material 212 may be disposed in the lumen of the tube before or after inserting the flexible bristles 220.

In certain embodiments, the filler material 212 may be a curable or settable material such that after disposing the filler material 212 in the lumen of the tube, the filler material 212 is cured or set such that it hardens so as to secure the plurality of flexible bristles 220 to the stem 210.

Figure 5:
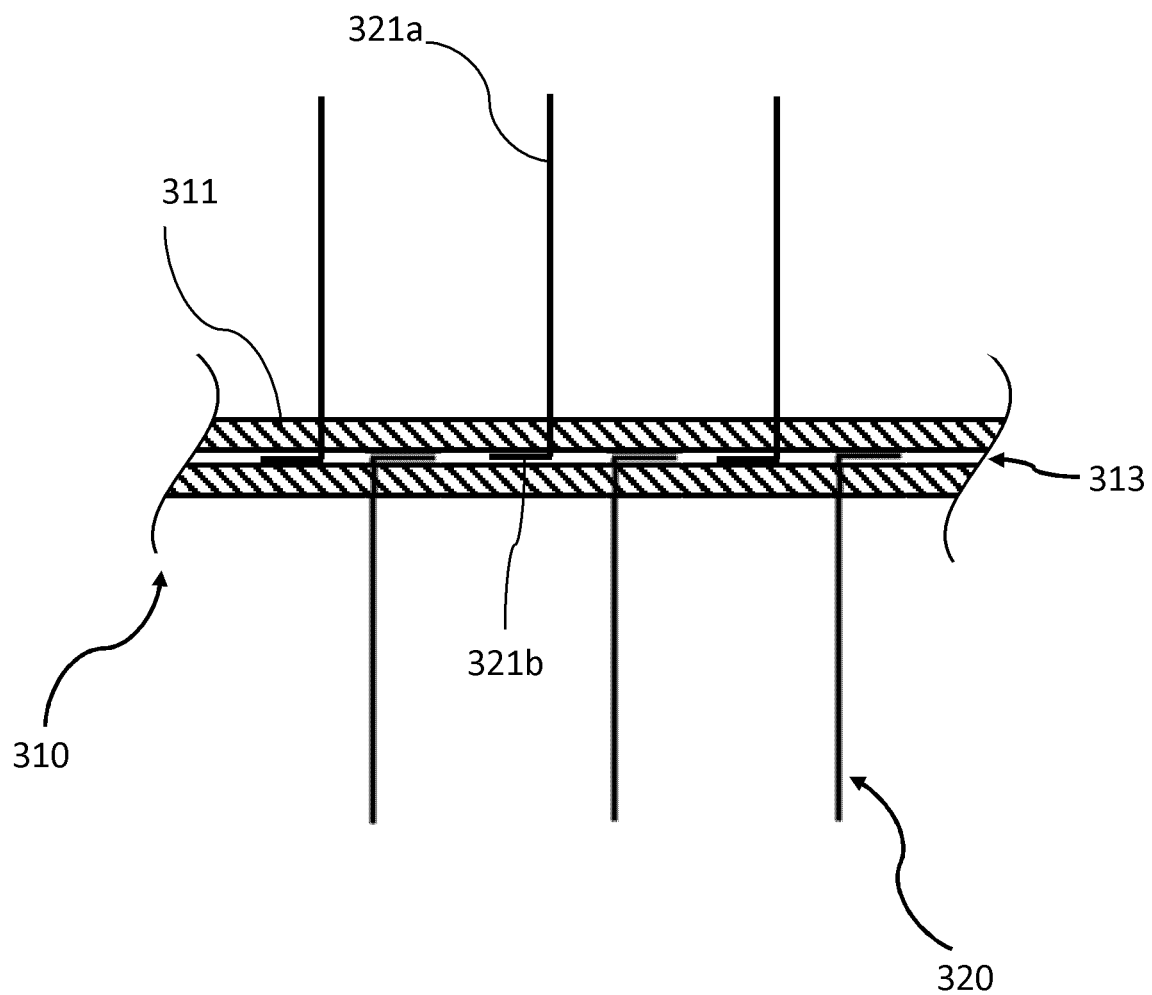

FIG. 5 shows a cross-section along part of the length of an embodiment of the embolization device, and, in particular, the stem 310 and flexible bristles 320.

The stem 310 of the embolization device comprises a tube having a tube wall 311.

As can be seen from FIG. 5, each of the plurality of flexible bristles 320 penetrate through the tube wall 311. A free portion 321a of each of the plurality of flexible bristles 220 extends radially outwardly from the tube, and, in particular, the tube wall 311.

A clamped portion 321b of each of the plurality of flexible bristles 320 is clamped between two opposing sides of the tube wall 311. The opposing sides of the tube wall 311 provide a clamping force on each of the clamped portions 321b such that the flexible bristles 320 are secured to the stem 310.

In the embodiment shown in FIG. 5, the tube of the stem 310 has a lumen 313 extending along substantially the entire length of the tube. In this embodiment, the lumen 313 is a continuous lumen in which the clamped portions 321b of the flexible bristles 320 are disposed within the lumen 313. The opposing sides of the tube wall 311 may not contact each other at regions between the clamped portions 321b such that a continuous lumen is defined.

One portion of the lumen 313 may not be in fluid communication with another portion of the lumen 313, for example, due to a clamped portion 321b entirely filling a section of the lumen 313.

In certain embodiments, the portions of the tube wall 311 between some or all of the clamped portions 321b may be configured such that the opposing sides of the tube wall 311 contact each other (not shown in FIG. 5).

Optionally, the portions of the tube wall 311 of the tube between each of the clamped portions 321b may be configured such that the opposing sides of the tube wall 311 contact each other such that the tube may comprise a number of distinct, isolated lumens disposed along the length of the tube. The lumens of the tube may be substantially filled by the clamped portions 321b of the plurality of flexible bristles 320.

The lumen(s) 313 of the tube may be filled with any filler material disclosed herein, such as the filler material 212 of FIG. 4.

The stem 310 and flexible bristles 320 of the embolization device may be manufactured by creating, for example, by machining, a plurality of holes in the tube wall 311 of the tube. One or some of the plurality of flexible bristles 320 may be inserted through each of the plurality of holes in the tube wall 311 such that a portion 321b of each of the flexible bristles 320 extends into the lumen 313 of the tube.

The portions 321b of each of the flexible bristles 320 may be clamped between two opposing sides of the tube wall 311.

In this regard, at least portions of the tube may be shrunk, for example, heat shrunk or chemically shrunk, in a radial direction such that the portions 321b of each of the flexible bristles 320 are clamped between two opposing sides of the tube wall 311.

Additionally or alternatively, at least portions of the tube may be compressed (e.g. mechanically compressed), for example, by crimping, in a radial direction such that the portions 321b of each of the flexible bristles 320 are clamped between two opposing sides of the tube wall 311.

Figure 6:
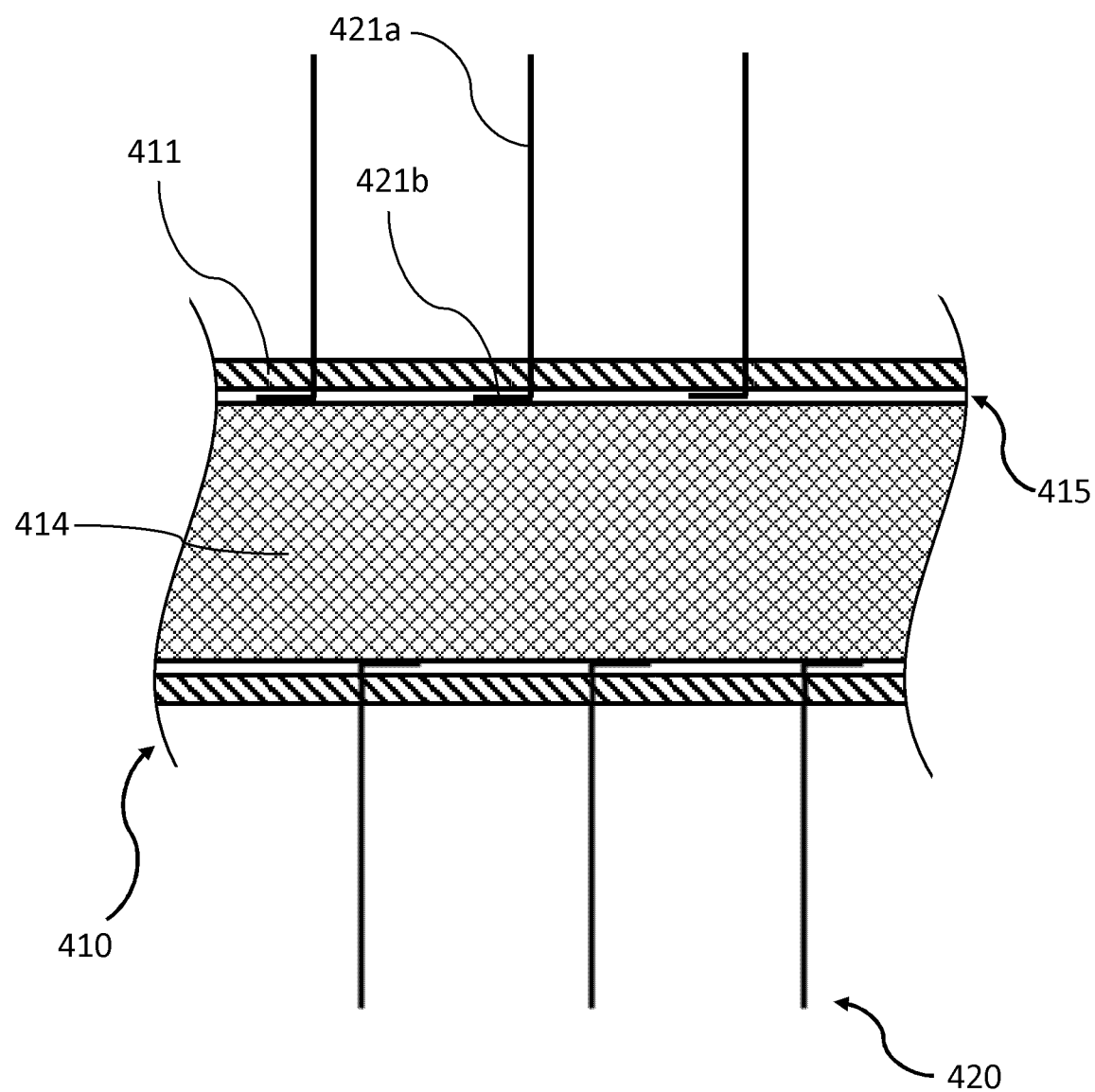

FIG. 6 shows a cross-section along part of the length of an embodiment of the embolization device, and, in particular, the stem 410 and flexible bristles 420.

The stem 410 of the embolization device comprises a tube having a tube wall 411.

As can be seen from FIG. 6, each of the plurality of flexible bristles 420 penetrates through the tube wall 411. A free portion 421a of each of the plurality of flexible bristles 420 extends radially outwardly from the tube, and, in particular, the tube wall 411.

A clamped portion 421b of each of the plurality of flexible bristles 420 is clamped between an inner mandrel 414 disposed within the lumen of the tube and the tube wall 411.

The clamped portions 421b of each of the flexible bristles 420 may be disposed within an annulus 415 defined between the inner mandrel 414 and the tube wall 411.

The outer surface of the inner mandrel 414 and the inner surface of the tube wall 411 provide a clamping force on each of the clamped portions 421b such that the flexible bristles 420 are secured to the stem 410.

The portions of the tube wall 411 between some or all of the clamped portions 421b may be configured such that the outer surface of the inner mandrel 414 and the inner surface of the tube wall 411 contact each other (not shown in FIG. 6).

Optionally, the portions of the tube wall 411 between some or all of the clamped portions 421b may be configured such that the outer surface of the inner mandrel 414 and the inner surface of the tube wall 411 contact each other such that the stem 410 defines a number of distinct, isolated annuluses disposed along the length of the tube. The annuluses of the stem 410 may be substantially filled by the clamped portions 421b.

The annulus 313 or annuluses of the stem 410 may be filled with any filler material disclosed herein, such as the filler material 212 of FIG. 4.

The stem 410 and flexible bristles 420 of the embolization device may be manufactured by creating, for example, by machining, a plurality of holes in the tube wall 411 of the tube. One of the plurality of flexible bristles 420 may be inserted through each of the plurality of holes in the tube wall 411 such that a portion 421b of each of the flexible bristles 420 extends into the lumen of the tube.

An inner mandrel 414 may be inserted into the lumen of the tube such that the portions 321b are clamped between the inner mandrel 414 and the tube wall 411. Optionally, the tube wall 411 of the tube may be shrunk or mechanically compressed and/or the inner mandrel 414 may be radially expanded once it has been inserted into the lumen of the tube.

Figure 7:
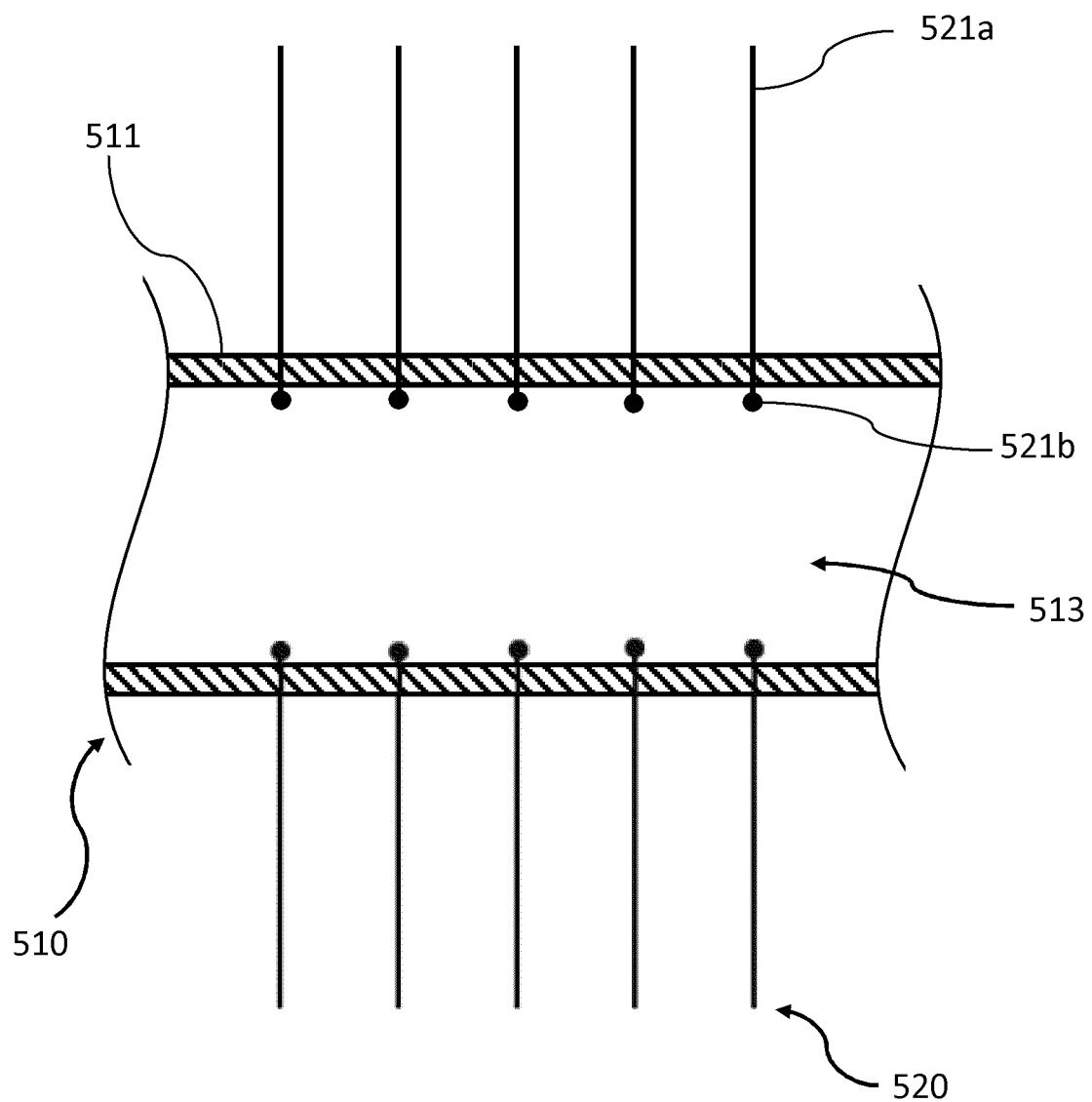

FIG. 7 shows a cross-section along part of the length of an embodiment of the embolization device, and, in particular, the stem 510 and flexible bristles 520.

The stem 510 of the embolization device comprises a tube having a tube wall 511.

Each of the plurality of flexible bristles 520 penetrates through the tube wall 511 such that a portion 521b is disposed within the lumen 513 of the tube. A free portion 521a of each of the plurality of flexible bristles 520 extends radially outwardly from the tube, and, in particular, the tube wall 511.

As shown in FIG. 7, the portion 521b disposed within the lumen 513 of the tube is thicker than the free portion 521a. The portion 521b may be configured such that the flexible bristle is secured to the tube. Specifically, the portion 521b may have a larger radius than the radius of a hole in the tube wall 511 through which the flexible bristle passes.

Additionally or alternatively, the portion 521b disposed within the lumen 513 of the tube may comprise a rough portion. The rough portion may be rougher than some or all portions of the free portion 521a.

The lumen 513 of the stem 510 may be filled with any filler material disclosed herein, such as the filler material 212 of FIG. 4.

Additionally or alternatively, some or all of the portions 521b may be clamped between two opposing sides of the tube wall 511, in a similar manner as described in relation to FIG. 5.

Additionally or alternatively, some or all of the portions 521b may be clamped between an inner mandrel (not shown) disposed within the lumen 513 of the tube and the tube wall 511, in a similar manner as described in relation to FIG. 6.

The stem 510 and flexible bristles 520 of the embolization device may be manufactured by creating, for example, by machining, a plurality of holes in the tube wall 511 of the tube. One of the plurality of flexible bristles 520 may be inserted through each of the plurality of holes in the tube wall 511 such that a portion 521b of each of the flexible bristles 520 extends into the lumen 513 of the tube.

For example, a guide may be inserted into the lumen 513 of the tube such that the free portion 521a may be guided from the inside of the lumen 513 through the hole to the outside of the tube.

Additionally or alternatively, the tube may have a thin slit along at least a portion of its length so as to facilitate insertion of the flexible bristles 520 through their respective holes from the inside of the lumen.

In the embodiments described with reference to FIGS. 4 to 7, an end of the flexible bristles terminates within the tube of the stem. However, some or all of the flexible bristles of the embodiments described with reference to FIGS. 4 to 7 may extend through the stem such that both ends of the flexible bristles are exterior to the stem. The means and methods described in relation to FIGS. 4 to 7 are equally applicable to such embodiments.

Figure 8:
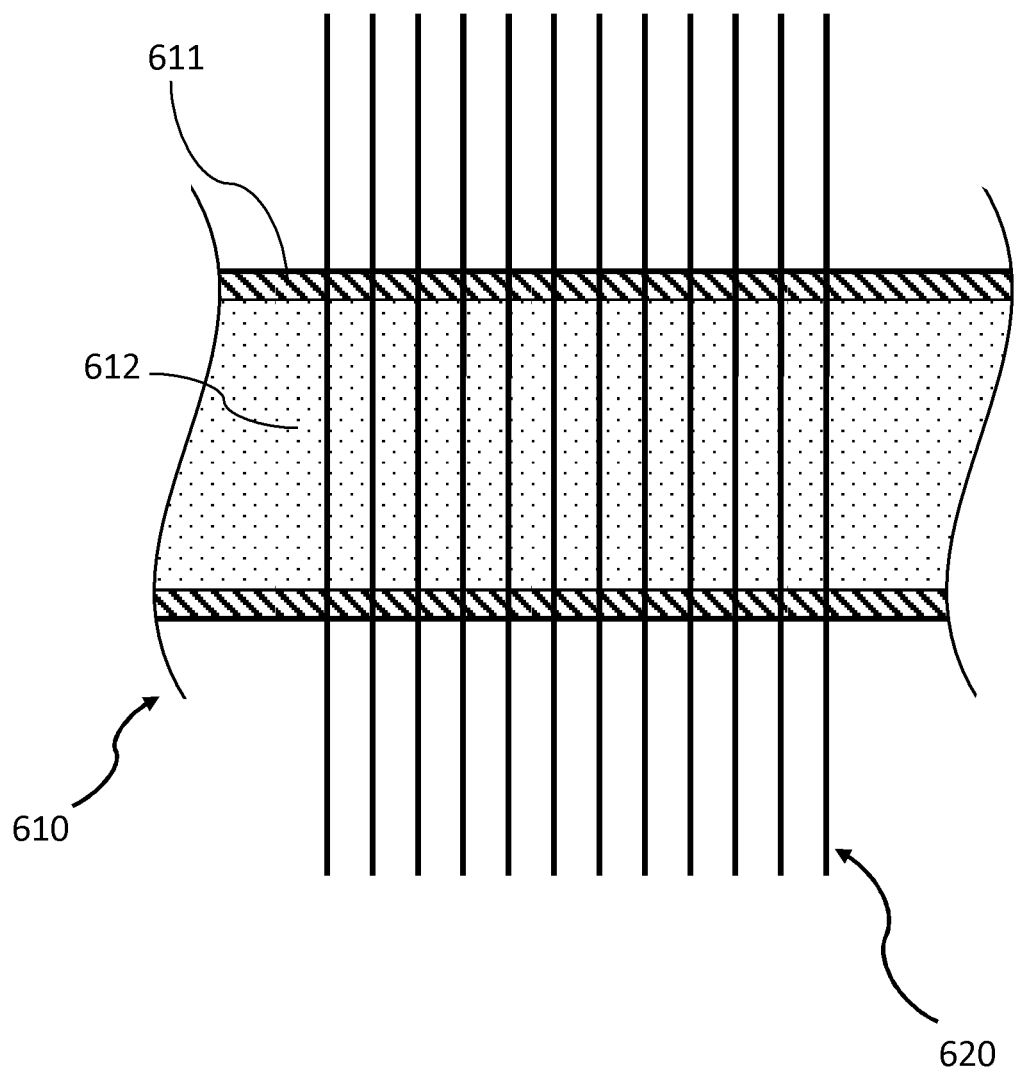

For example, FIG. 8 shows a cross-section along part of the length of an embodiment of the embolization device, and, in particular, the stem 610 and flexible bristles 620.

As in the previous embodiments, the embolization device comprises a tube having a tube wall 611. The plurality of flexible bristles 620 each penetrate through the tube wall 611 at a first location and at a second location. Both of the ends of the flexible bristles 620 are disposed outside the tube of the stem. Both ends extend radially outwardly from the tube, and, in particular, the tube wall 611.

In the embodiment shown in FIG. 8, the stem 610 further comprises filler material 612 disposed within the lumen of the tube in a similar manner to that described in relation to FIG. 4. However, as noted above, any means or methods described herein are suitable for securing the flexible bristles 620 to the stem.

The above-noted first location and second location may be chosen in various manners.

Figure 9:
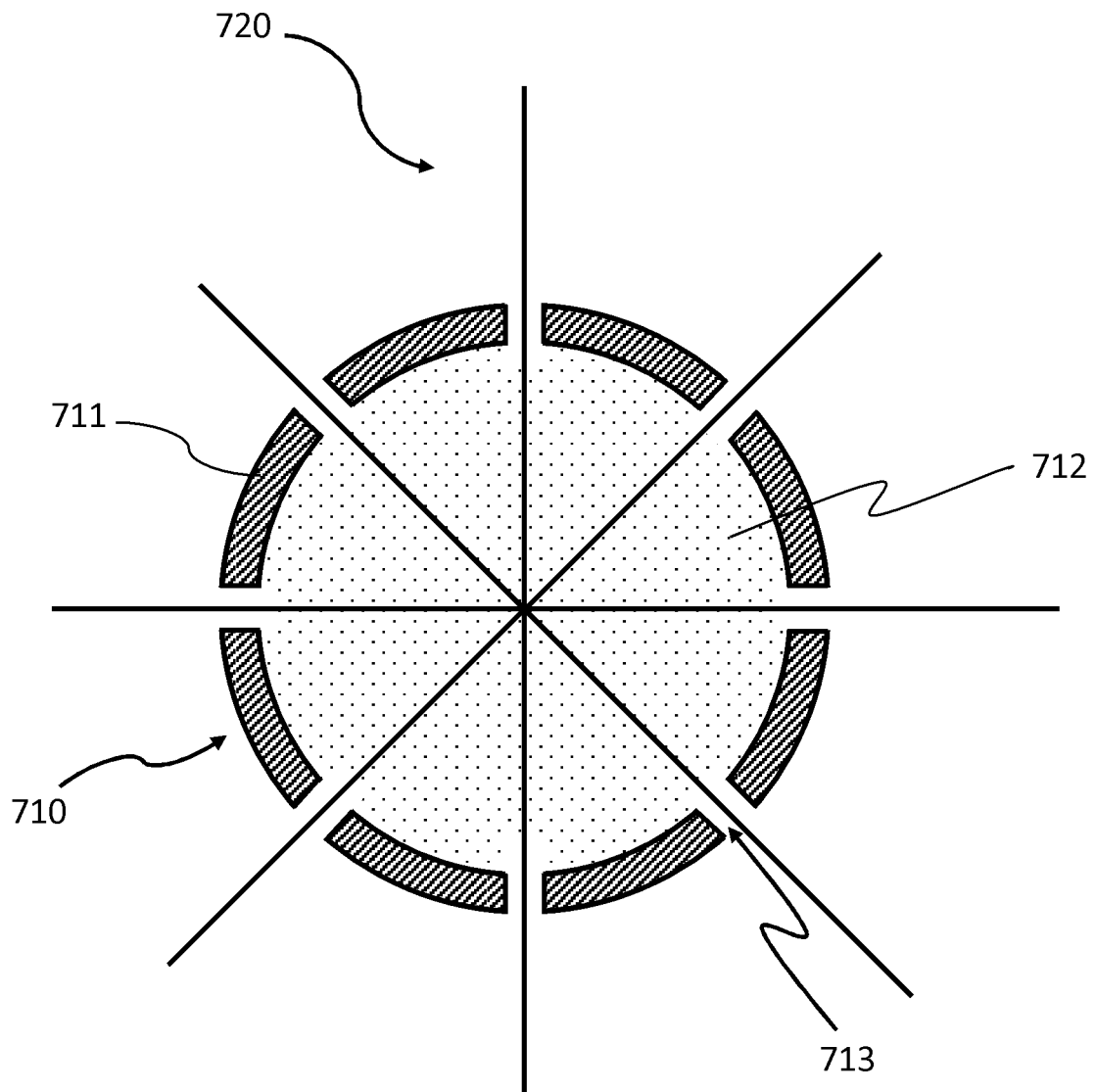
FIGS. 9 and 10 each show a transverse cross-section along the length of certain embodiments of the embolization device.

In this regard, reference is made to FIG. 9 which shows a transverse cross-section along the length of an embodiment of the embolization device, and, in particular, the stem 710 and flexible bristles 720.

As can be seen from FIG. 9, each of the flexible bristles 720 passes through holes 713 at first and second locations in the tube wall 711. In a similar manner as above, purely as an example, the stem 710 further comprises filler material 712 disposed within the lumen of the tube to secure the flexible bristles 720 to the stem 710.

The first and second locations of the holes 713 are on substantially opposite sides of the circumference of the tube.

Figure 10:
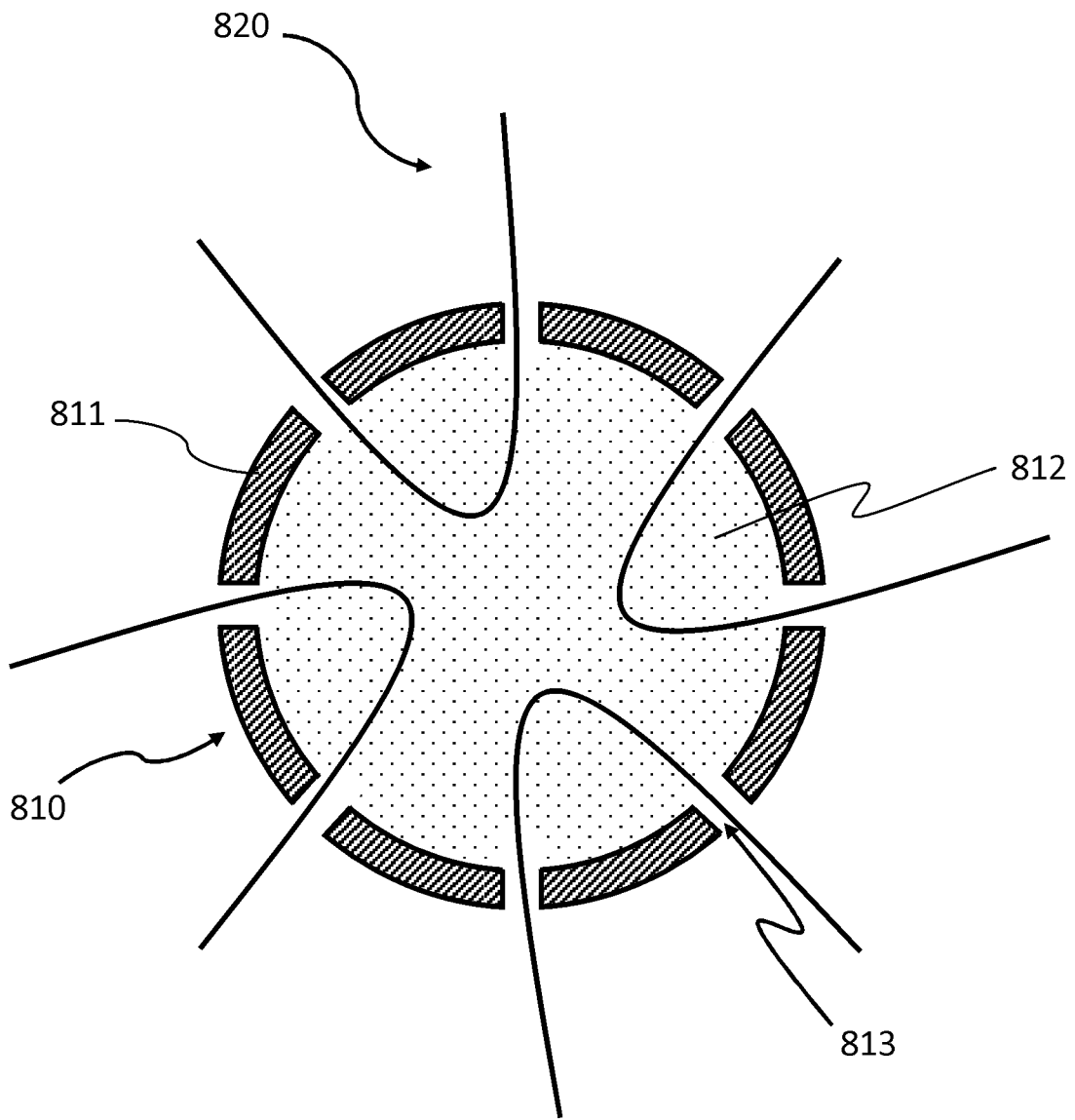

FIG. 10 shows a transverse cross-section along the length of another embodiment of the embolization device, and, in particular, the stem 810 and flexible bristles 820.

Each of the flexible bristles 820 passes through holes 813 at first and second locations in the tube wall 811. In a similar manner as above, purely as an example, the stem 810 further comprises filler material 812 disposed within the lumen of the tube to secure the flexible bristles 820 to the stem 810.

As can be seen from FIG. 10, the first and second locations of the holes 813 are in the same quarter of the circumference of the stem. In other embodiments, the first and second locations of the holes 813 are in the same half, third, fifth or sixth of the circumference of the stem.

Optionally, the first and second locations of the holes 713 are substantially axially aligned.

The flexible bristles 720, 820 may be inserted through the holes at the first and second locations using a guide disposed within the lumen of the tube.

Additionally or alternatively, the tube may have a thin slit along at least a portion of its length so as to facilitate insertion of the flexible bristles 720, 820 through their respective holes at the first and second locations.

Figure 11:
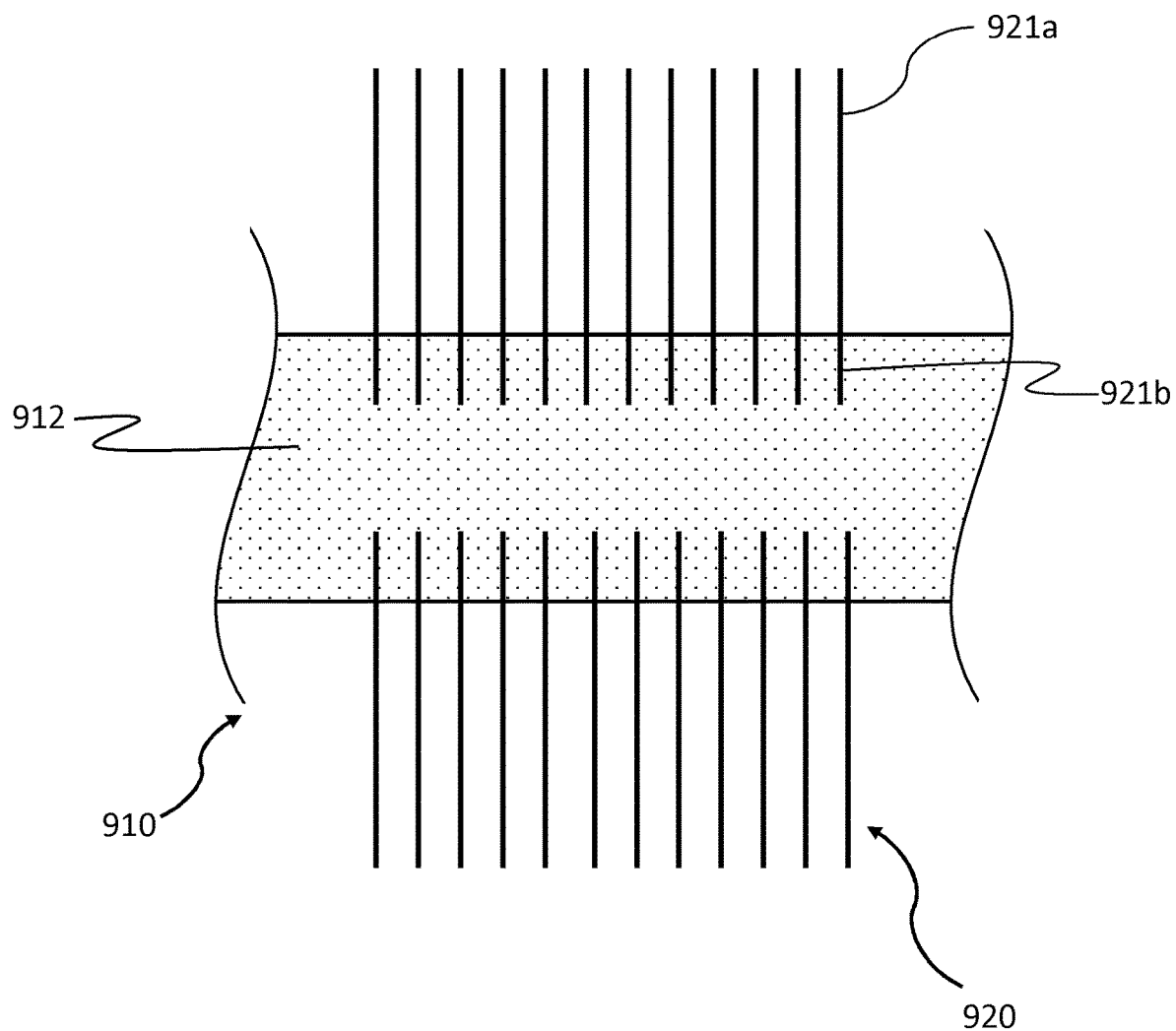
FIGS. 11 to 13 each show a cross-section along part of the length of various embodiments of the embolization device.

FIG. 11 shows a cross-section along part of the length of an embodiment of the embolization device, and, in particular, the stem 910 and flexible bristles 920.

The plurality of flexible bristles 920 extend radially outwardly from the stem 910. In particular, a free portion 921a of each of the plurality of flexible bristles 920 extends radially outwardly from the stem 910.

The stem 910 is formed from a material 912. A portion 921b of each of the flexible bristles 920 is disposed within a volume of the material 912 of the stem 910. The material 912 surrounds the portion 921b and secures the portion 921b to the stem 910.

As shown in FIG. 11, the material 912 substantially entirely surrounds and contacts an end portion 921b of each of the flexible bristles 920. Specifically, the material 912 may contact substantially an entire transversely extending edge surface of each of the flexible bristles 920.

Referring to FIG. 11, the volume of the material 912 is a bulk or homogenous volume of the stem 910 formed from a continuous volume of the material 912.

The material 912 of the stem 910 engages the portions 921b of the flexible bristles 920. The material 912 acts to secure the plurality of flexible bristles 920 to the stem 910.

The material 912 may be an adhesive. In such embodiments, the material 912 may engage the portions 921b of the flexible bristles 910 by adhering or bonding to the portions 921b.

The material 912 may be a curable material or settable material, which is curable or settable upon heating, solvent flashing and/or irradiating. Upon curing or setting, the material may harden so as to secure the flexible bristles 920 to the stem 910.

The material 912 may engage the portions 921b of the flexible bristles 920 to mechanically anchor the flexible bristles 920 to the stem 910.

As one (or a sub-set) of the plurality of flexible bristles 920 passes into the material of the stem 910, the flexible bristles 920 are attached to the stem individually or in a (small) sub-set. Accordingly, if the integrity of the attachment of one of the flexible bristles becomes compromised, the integrity of the attachments of the other flexible bristles may not be compromised. For example, if one of the plurality of flexible bristles 920 is dislodged from the stem 910, the attachment of the remaining flexible bristles may remain uncompromised, which is not the case when the majority of the attachment force for a particular bristle is provided for by surrounding/neighbouring bristles.

Furthermore, the material 912 may be chosen so as to influence the structural properties of the stem 910, for example, flexibility.

The stem 910 and flexible bristles 920 of the embolization device may be manufactured by providing a stem 910 formed from a material 912 and providing a plurality of flexible bristles 920 such that a portion 921b of each of the flexible bristles 920 is disposed within a volume of the material 912.

For example, the portions 921b of the flexible bristles 920 may be inserted into the material 912. Thereafter, the material 912 may be cured or set such that the material 912 surrounds the portions 921b and secures the portions 921b to the stem 910, for example, by the hardening and/or contraction of the material 912.

In certain embodiments, the stem 910 may be formed by molding the material 912. For example, the portions 921b of the flexible bristles 920 may be inserted into a mold cavity defined by a mold. A material to be molded may be inserted into the mold cavity. The material may be allowed to set such that the material 912 surrounds and secures the flexible bristles 920. The mold may then be removed to leave the stem 910 and flexible bristles 920 secured thereto.

In certain embodiments, a mold is not required. For example, the material 912 may be shaped into the stem 910. Thereafter, the plurality of flexible bristles 920 may be inserted into the shaped material 912 such that the portions 921b are disposed within a volume of the material 912. Thereafter, the material 912 may optionally be cured or set such that the material 912 surrounds the portions 921b and secures the portions 921b to the stem 910, for example, by the hardening and/or contraction of the material 912.

Figure 12:
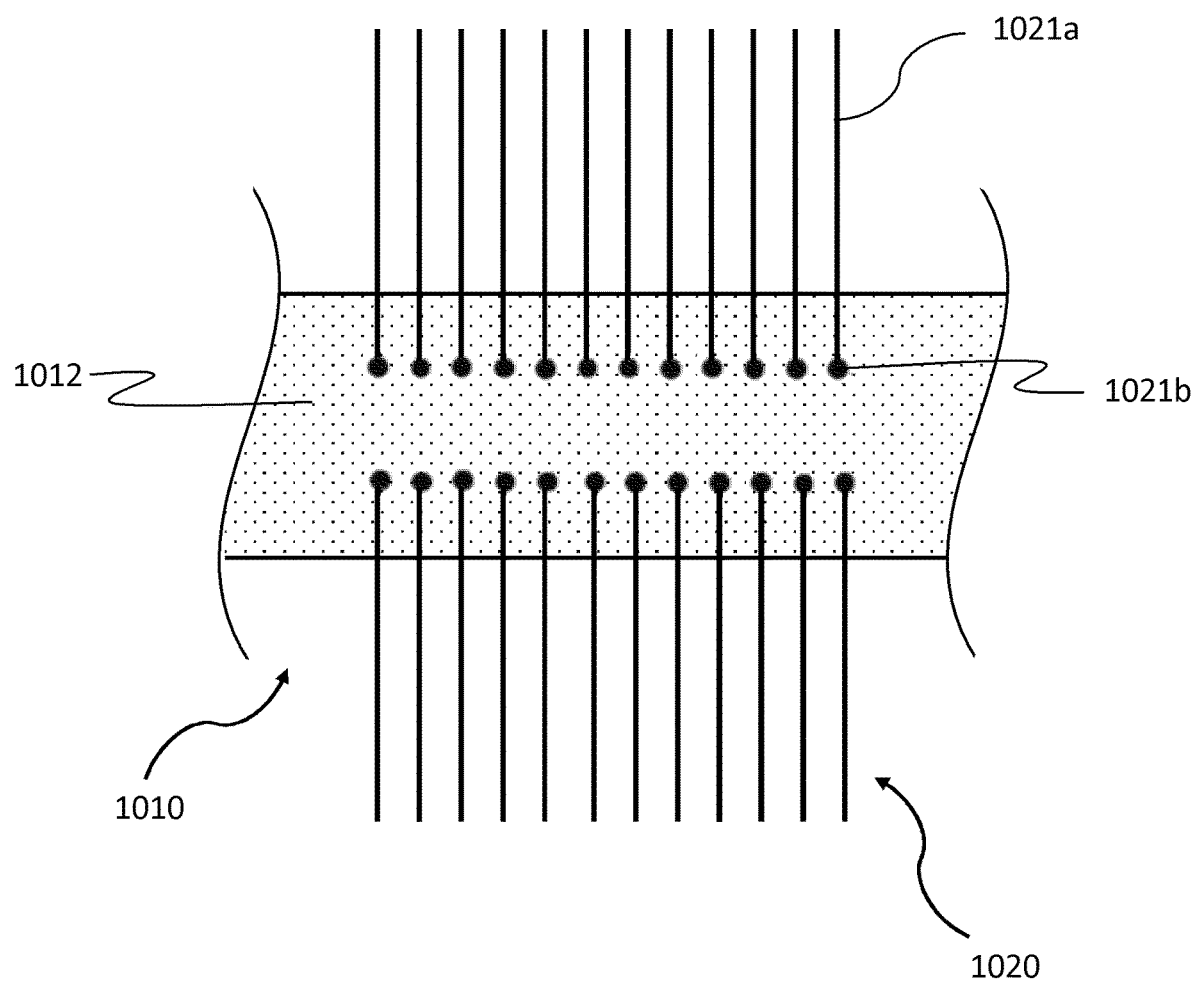

FIG. 12 shows a cross-section along part of the length of an embodiment of the embolization device, and, in particular, the stem 1010 and flexible bristles 1020.

The embodiment shown in FIG. 12 is similar to the embodiment of FIG. 11 in that the embolization device has a stem 1010 formed from a material 1012, and where a portion 1021b of each of the flexible bristles 1020 is disposed within a volume of the material 1012 and a free portion 1021a extends radially outwardly.

However, in the embodiment shown in FIG. 12, the portion 1021b is thicker than the free portion 1021a. For example, the portion 1021b may include a spherical anchoring section. Additionally or alternatively to the thickened region, the portion 1021b may comprise a rough region (not shown). The rough region may be rougher than some or all portions of the free portion 1021a.

The forms of the flexible bristles 1020 are generally applicable to all embodiments described herein.

Figure 13:
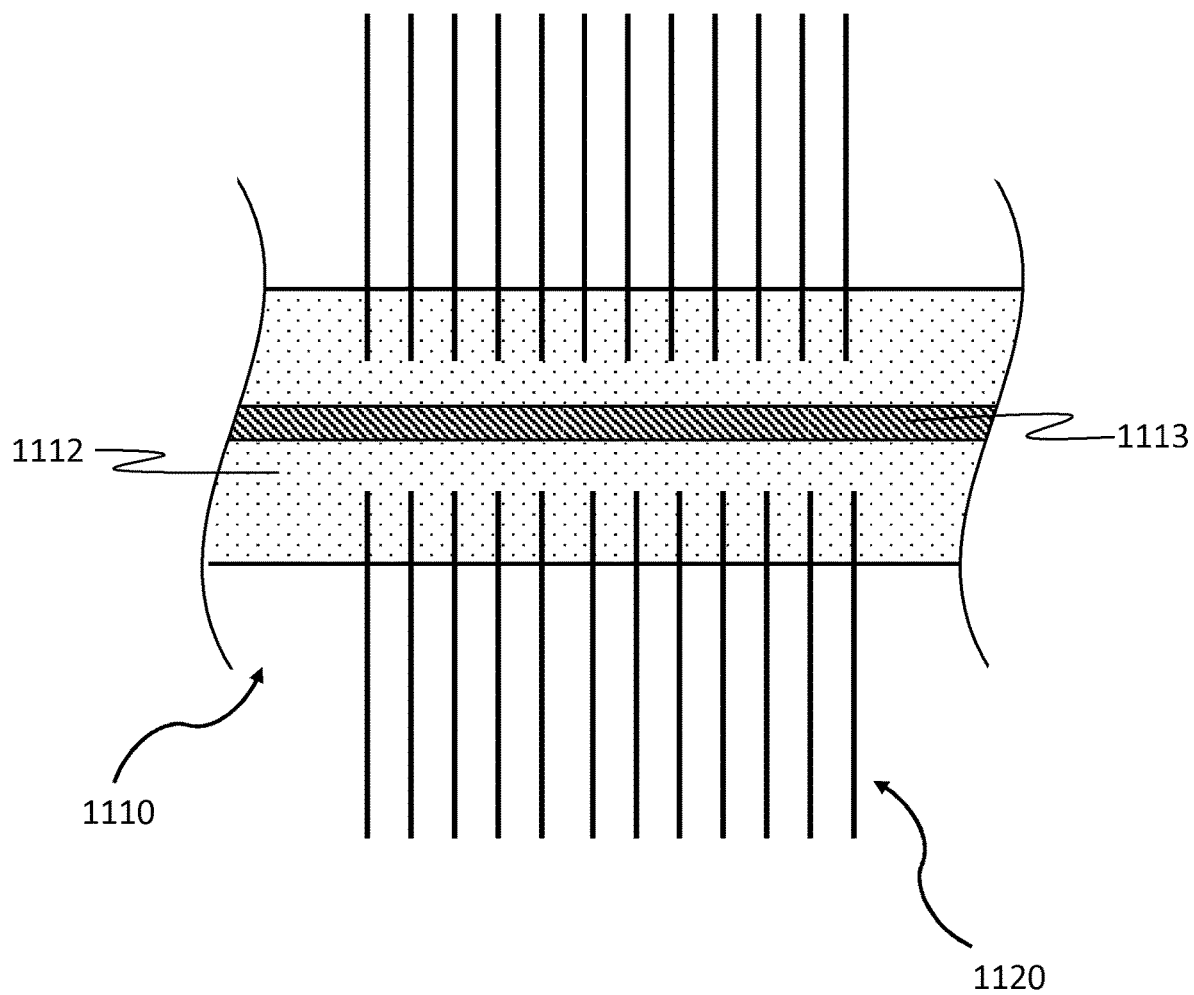

FIG. 13 shows a cross-section along part of the length of an embodiment of the embolization device, and, in particular, the stem 1110 and flexible bristles 1120.

The embodiment shown in FIG. 13 is similar to the embodiment of FIG. 11 in that the embolization device has a stem 1110 formed from a material 1112, and where a portion of each of the flexible bristles 1120 is disposed within a volume of the material 1112 and a free portion extends radially outwardly.

However, in the embodiment shown in FIG. 13, the stem 1110 further comprises a structural member 1113. The structural member 1113 may be disposed at least partially or entirely within the material 1112 of the stem 1110.

The structural member 1113 may extend longitudinally along the length of the stem 1110. The structural member 1113 may be elongated or rod-shaped.

The structural member 1113 may be disposed within the material 1112 before the material 1112 is cured or set so as to secure the structural member 1113 within the material 1112 of the stem. Alternatively, the structural member 1113 may be disposed within the material 1112 by inserting it into the material 112 after it has been cured or set, for example, by boring a hole within the material 1112 using the structural member 1113 itself and/or another device, such as a drill.

Figure 14:
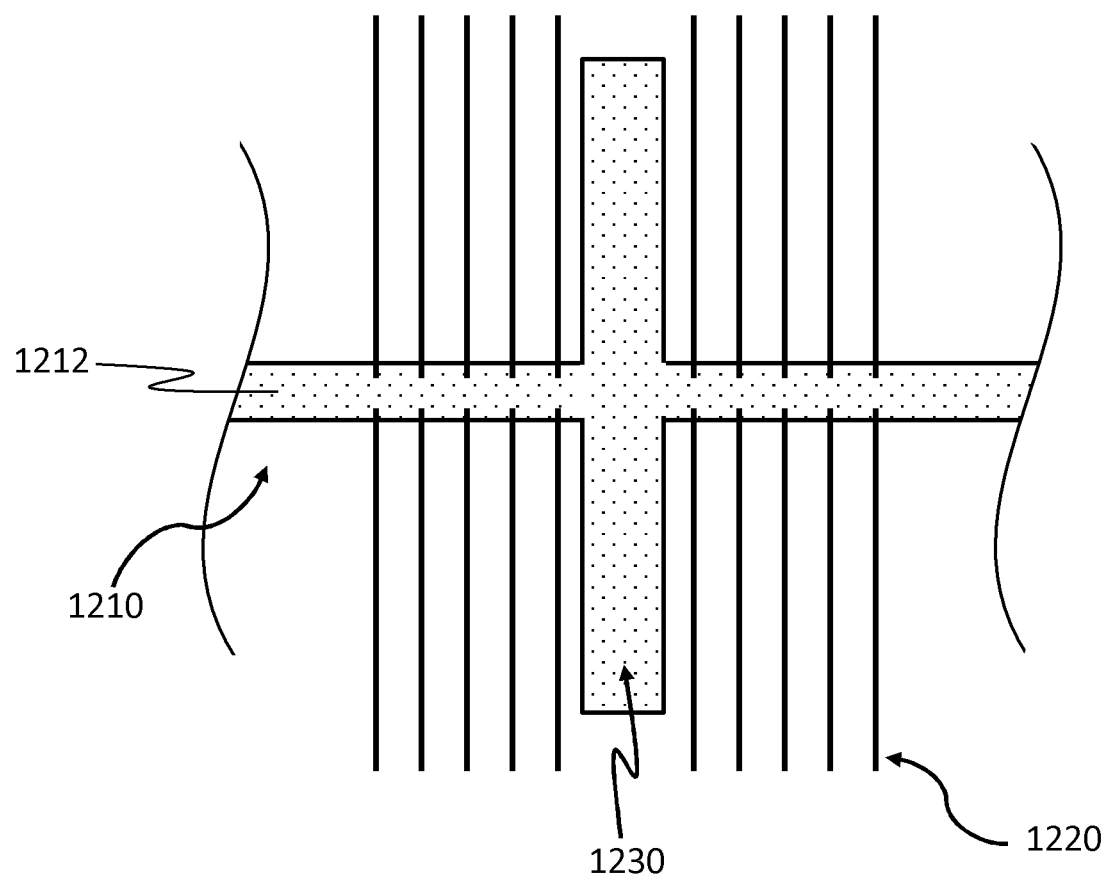
FIGS. 14 to 16 each show a cross-section along part of the length of various embodiments of the embolization device which comprise a flow restricting membrane.

FIG. 14 shows a cross-section along part of the length of an embodiment of the embolization device, and, in particular, the stem 1210, flexible bristles 1220 and flow restricting membrane 1230.

The embodiment shown in FIG. 14 is similar to the embodiment of FIG. 11 in that the embolization device has a stem 1210 formed from a material 1212, and where a portion of each of the flexible bristles 1220 is disposed within a volume of the material 1212 and a free portion extends radially outwardly.

However, as can be seen from FIG. 14, the embolization device further comprises a flow restricting membrane 1230. The flow restricting membrane may extend radially outwardly from the stem 1210.

The flow restricting membrane 1230 is formed from the same material 1212 as the stem 1210. The flow restricting membrane 1230 is integrally formed with the material 1212 of the stem.

As the stem 1210 and the flow restricting membrane 1230 are formed integrally, the above-noted issues relating to the attachment of a separate membrane to a core may be avoided.

The stem 1210, flexible bristles 1220 and flow restricting membrane 1230 may be manufactured by providing a stem 1210 and flow restricting membrane 1230 formed integrally from the material 1212, and providing a plurality of flexible bristles 1220 such that a portion 1221b of each of the flexible bristles 1220 is disposed within a volume of the material 1212.

For example, the stem 1210 and flow restricting membrane 1230 may be formed by molding the material 1212. In this regard, a continuous mold cavity defined in a single mold may have a shape which defines the stem 1210 and the flow restricting membrane 1230 connected thereto. The portions 1221b of the flexible bristles 1220 may be inserted into the mold cavity by inserting them through holes defined in the mold. A moldable material may be disposed in the mold cavity and allowed to set such that the material 1212 take the form of the stem 1210 and the flow restricting membrane 1230 connected thereto. The material 1212 also sets to surround and secure the flexible bristles 1220. The mold may then be removed to leave the stem 1210, the flexible bristles 1220 secured thereto, and the flow restricting membrane 1230.

In certain embodiments, a mold is not required. For example, the material 1212 may be shaped into the stem 1210 and flow restricting membrane 1230. Thereafter, as described above, the plurality of flexible bristles 1220 may be inserted into the shaped material 1212. Thereafter, the material 912 may optionally be cured or set.

Figure 15:
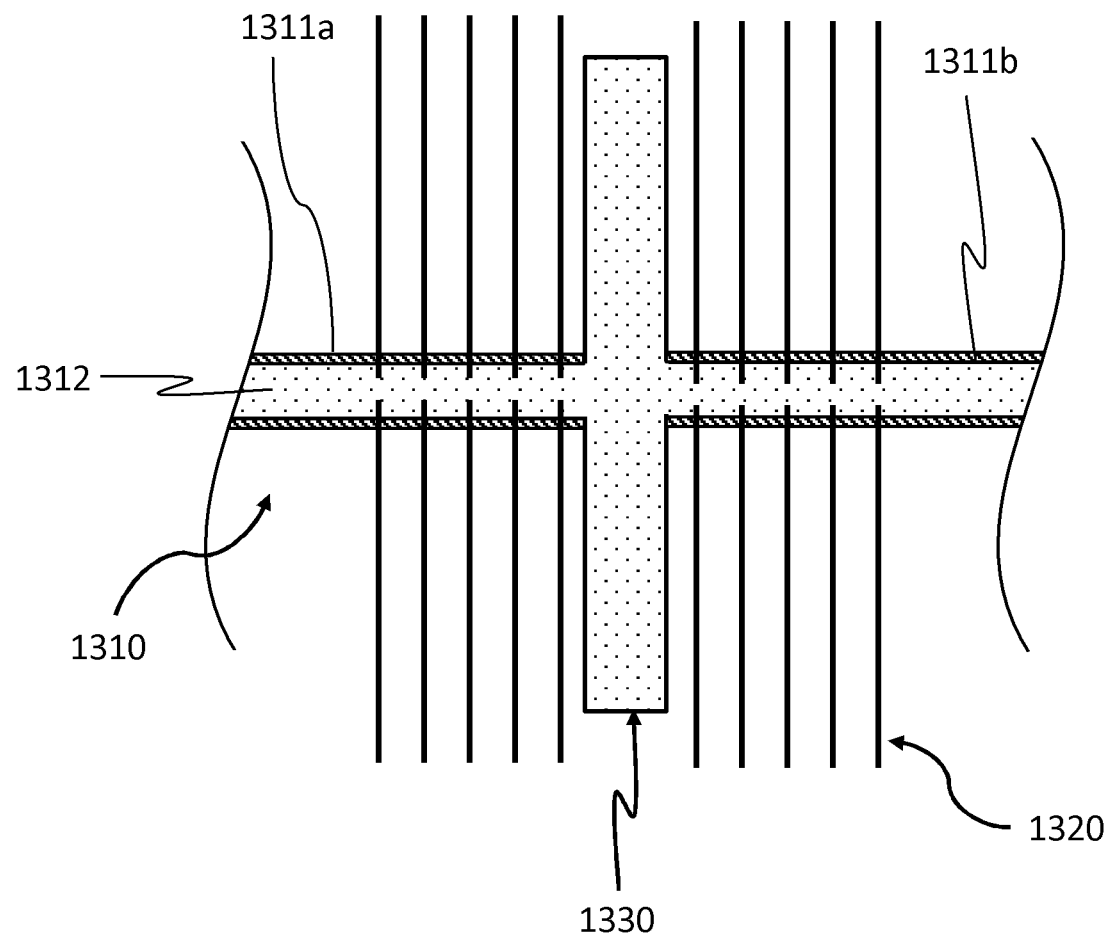

FIG. 15 shows a cross-section along part of the length of an embodiment of the embolization device, and, in particular, the stem 1310, flexible bristles 1320 and flow restricting membrane 1330.

The embodiment shown in FIG. 15 is similar to the embodiment of FIG. 14 in that the embolization device has a stem 1310 and flow restricting membrane 1330 formed integrally from a material 1312, and where a portion of each of the flexible bristles 1320 is disposed within a volume of the material 1312 and a free portion extends radially outwardly.

However, as can be seen from FIG. 15, the stem 1310 further comprises two tubes each having tube walls 1311a, 1311b, in a similar manner to the tube with tube wall 211 described in relation to FIG. 4. As can be seen from FIG. 15, the plurality of flexible bristles 1320 extend radially outwardly from the tubes, and, in particular, the tube walls 1311a, 1311b. The plurality of flexible bristles 1320 each penetrate through the respective tube walls 1311a, 1311b as detailed herein.

The tubes may be disposed on either side of the flow restricting membrane 1330.

The stem 1310, flexible bristles 1320 and flow restricting membrane 1330 may be manufactured in a similar manner to that described in relation to FIG. 14.

However, two tubes having tube walls 1311a, 1311b are disposed over the material 1312. In this regard, the tubes may form part of a mold used to mold the material 1312 which is not removed after molding.

In other embodiments, the tubes may be placed over the material 1312 of the stem 1310 once the material 1312 has been shaped by any means into the form of the stem 1310.

Figure 16:
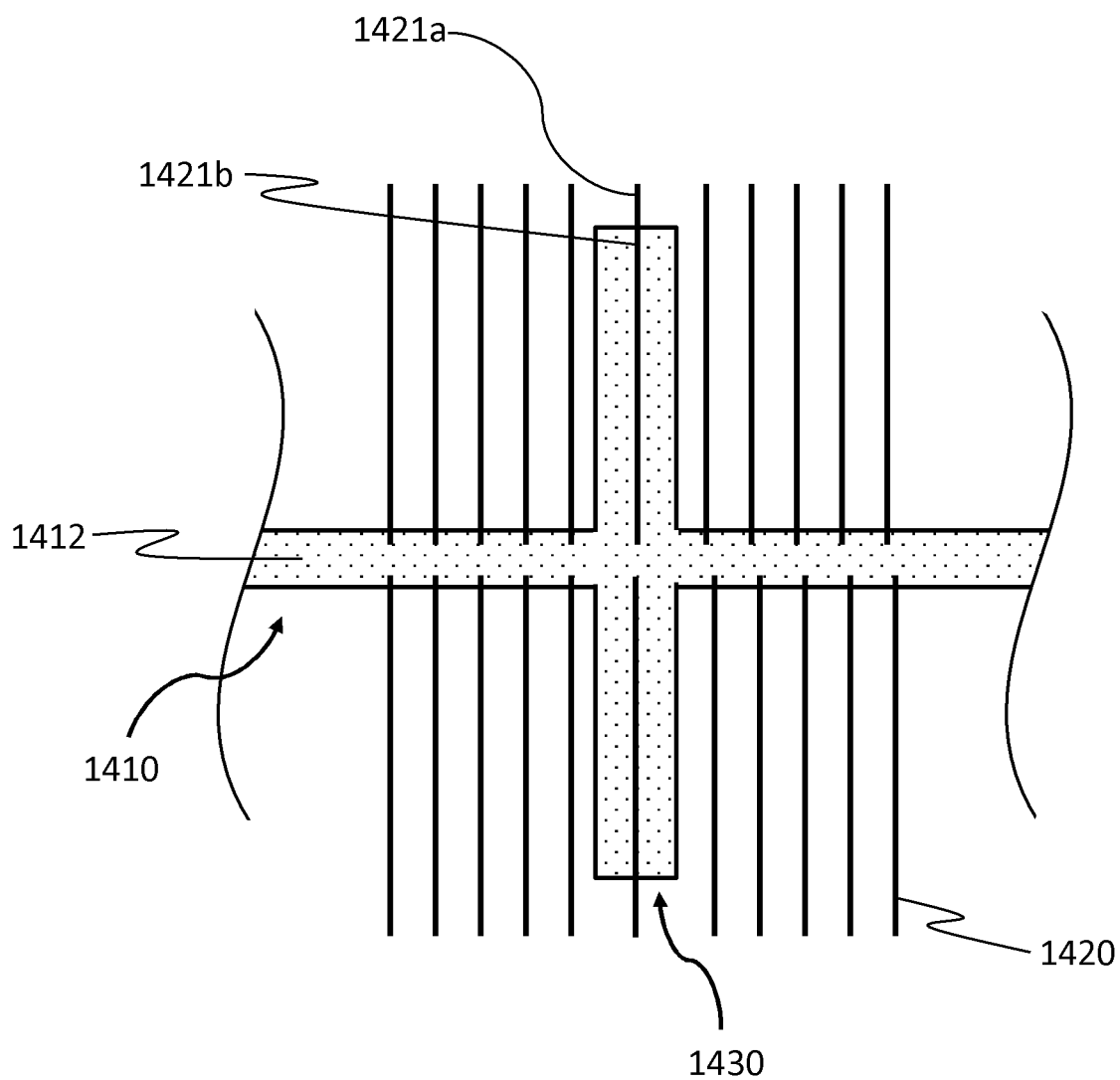

FIG. 16 shows a cross-section along part of the length of an embodiment of the embolization device, and, in particular, the stem 1410, flexible bristles 1420 and flow restricting membrane 1430.

The embodiment shown in FIG. 16 is similar to the embodiment of FIG. 14 in that the embolization device has a stem 1410 and flow restricting membrane 1430 formed integrally of a material 1412, and where a portion of each of the flexible bristles 1420 is disposed within a volume of the material 1412 and a free portion extends radially outwardly.

However, as can be seen from FIG. 16, a portion 1421b of at least one of the plurality of flexible bristles 1420 is disposed within a volume of the material 1412 of the flow restricting membrane 1430. The material 1412 of the flow restricting membrane 1430 may surround and secure the portion 1421b.

A free portion 1421a of the at least one of the plurality of flexible bristles 1420 extends freely radially outwardly from the flow restricting membrane 1430.

In certain embodiments, the entirety of the at least one of the plurality of flexible bristles 1420 is disposed within the within a volume of the material 1412 of the flow restricting membrane 1430. In such embodiments, no free portion extends radially outwardly from the flow restricting membrane 1430.

The bristles may provide certain structural characteristics (such as rigidity/flexibility) to the flow restricting membrane 1430, and may improve the integrity of the flow restricting membrane 1430 relative to the stem 1410.

The stem 1410, flexible bristles 1420 and flow restricting membrane 1430 may be manufactured in a similar manner to that described in relation to FIG. 14.

However, the at least one of the flexible bristles 1420 is received within a volume of the material 1412 of the flow restricting membrane 1430. In this regard, the at least one of the flexible bristles 1420 may be inserted into the mold through a hole formed in the mold such that it penetrates into the part of the cavity which defines the flow restricting membrane 1430. In other embodiments, the at least one of the flexible bristles 1420 may be inserted into the material of the flow restricting membrane after it has been formed.

In the embodiments described with reference to FIGS. 11 to 16, an end of the flexible bristles terminates within the stem and/or flow restricting membrane.

Figure 17:
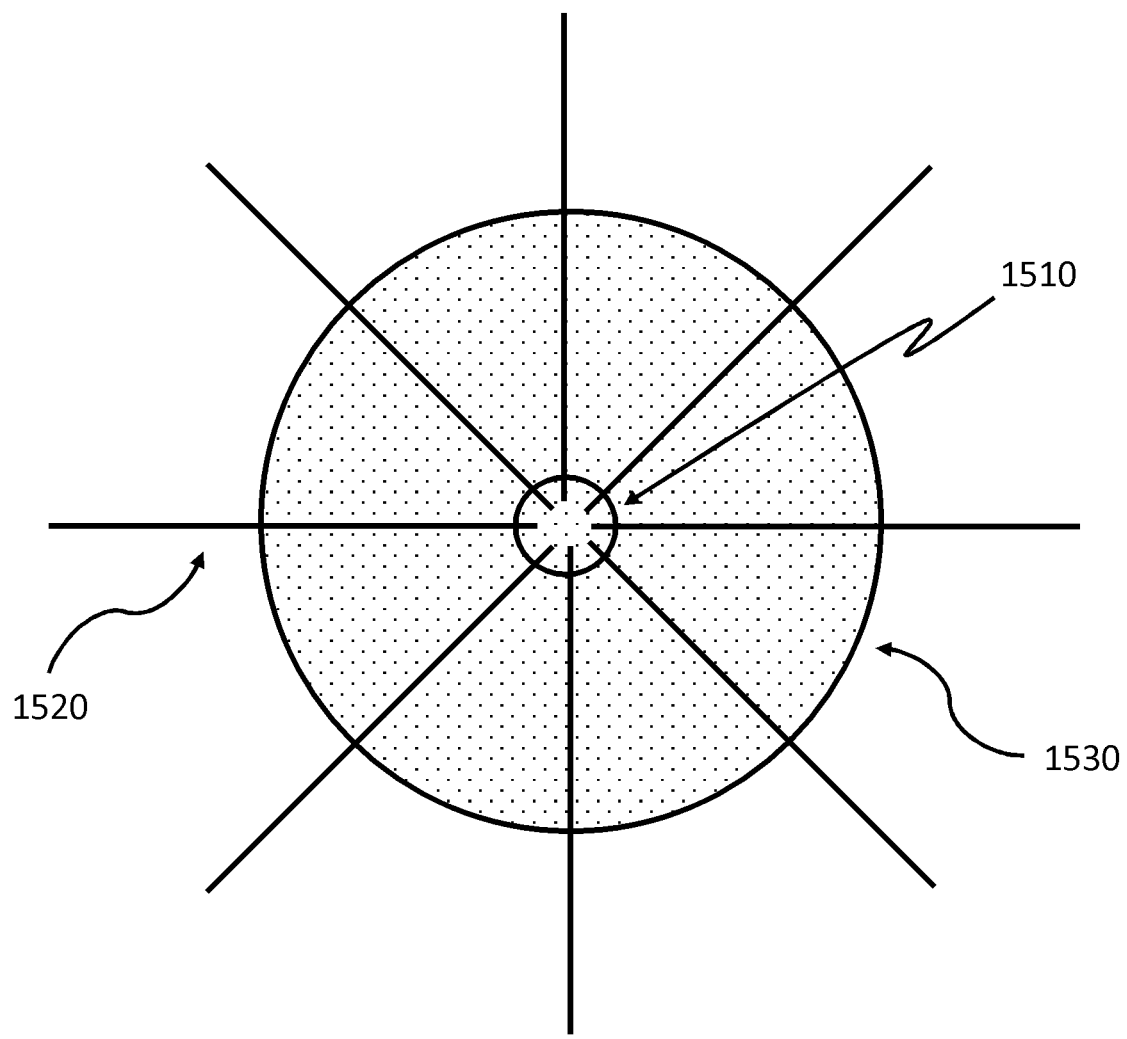
FIGS. 17 and 18 each show a transverse cross-section along the length of certain embodiments of the embolization device which comprise a flow restricting membrane.

In this regard, reference is made to FIG. 17 which shows a transverse cross-section along the length of an embodiment of the embolization device, and, in particular, the stem 1510, plurality of flexible bristles 1520 and flow restricting membrane 1530. As can be seen from this figure, each of the flexible bristles 1520 has an end section which is disposed within the stem 1510. In certain embodiments, some of the end sections of the flexible bristles 1520 may terminate within the flow restricting membrane 1530.

However, in other embodiments, some or all of the flexible bristles of the embodiments shown in FIGS. 11 to 16 may extend through the stem and/or flow restricting membrane such that both ends of the flexible bristles are exterior to the stem and/or flow restricting membrane. The means and methods described in relation to FIGS. 11 to 16 are equally applicable to such embodiments.

Figure 18:
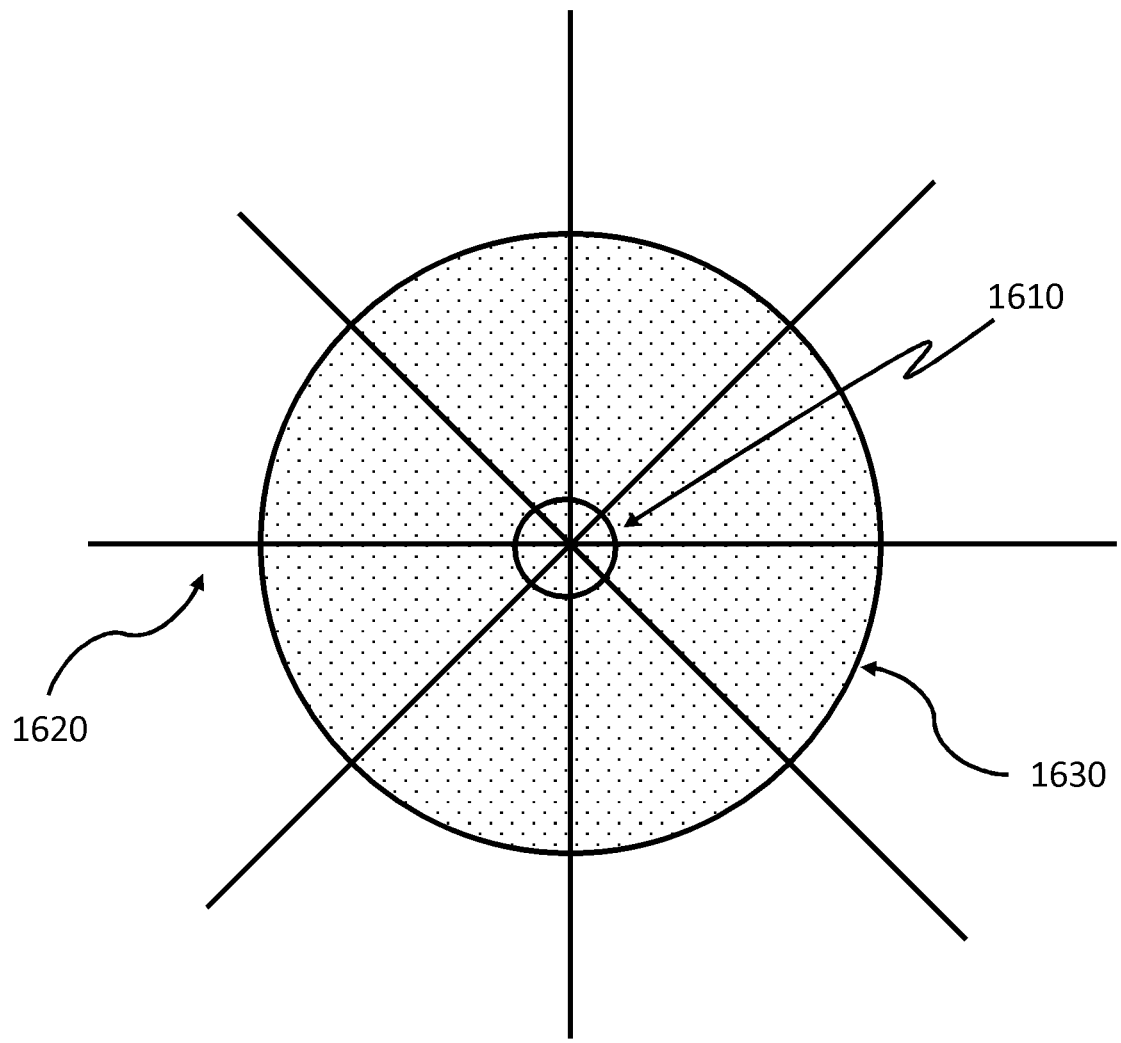

In this regard, reference is made to FIG. 18 which shows a transverse cross-section along the length of an embodiment of the embolization device, and, in particular, the stem 1610, plurality of flexible bristles 1620 and flow restricting membrane 1630. As can be seen from this figure, each of the flexible bristles 1520 passes through the stem 1610 and/or flow restricting membrane 1630.

Both of the ends of the flexible bristles 1620 are disposed outside the stem 1610 and/or flow restricting membrane 1630. Both ends extend radially outwardly from the stem 1610 and/or flow restricting membrane 1630.

As shown in FIG. 18, the each of the flexible bristles 1520 penetrates the surface of the stem 1610 and/or flow restricting membrane 1630 at a first location and a second location. The first and second locations of may be on substantially opposite sides of the circumference of the stem 1610 and/or flow restricting membrane 1630.

In a similar manner described in relation to FIG. 10, various arrangements of the first and second locations are contemplated. For example, the first and second locations of may be in the same quarter of the circumference of the stem 1610 and/or flow restricting membrane 1630. The first and second locations may be in the same half, third, fifth or sixth of the circumference of the stem 1610 and/or flow restricting membrane 1630.

Optionally, the first and second locations are substantially axially aligned.

FIGS. 17 and 18 show an embolization device with a flow restricting membrane, but the arrangements of the flexible bristles are equally applicable to embodiments without a flow restricting membrane.

Although the above explanation is considered to fully clarify how the present disclosure may straight-forwardly be put into effect by those skilled in the art, it is to be regarded as purely exemplary. In particular, there are a number of variations which are possible, as may be appreciated by those skilled in the art.

For example, even though the embodiments described in relation to FIGS. 4 to 10 show specific examples of securing the plurality of flexibles to the stem, such examples are preferred embodiments. Accordingly, any means of securing the plurality of flexibles to the stem, and, in particular, the tube is envisaged, so long as at least one of the plurality of flexible bristles penetrates through the tube wall of the tube.

Furthermore, even though the above embodiments have been described with all of the plurality of flexible bristles secured to the stem using the same means, it will be evident to the skilled person that not all of the plurality of flexible bristles need to be secured to the stem by the same means. Any combination of the above-noted means and methods may be used to attach the plurality of flexible bristles to the stem.

Further, even though the embodiment described in relation to FIG. 15 comprises two tubes 1311a, 1311b, any number of tubes may be used, including a single tube. Furthermore, the tubes may be any sort of covering element which is disposed on at least a portion of any outer surface of the material of the stem.

The above embodiments refer to a flow restricting membrane, however, other forms of flow restrictors are also envisaged in accordance with the present disclosure. In particular, any shape of flow restrictor is envisaged, so long as the flow restrictor acts to restrict flow in the bodily lumen L.

In the embodiments described in relation to FIGS. 14 to 18, at least of portion of each of the flexible bristles is disposed within the material of the stem and/or flow restrictor. However, this is optional. In particular, any means and methods, for example, conventional means and methods, may be used to secure the flexible bristles to the stem, and portions of the stem to which the flexible bristles are secured may be formed by conventional means and method, for example, using a twisted wire method, as described in WO 2014/140325 and WO 2016/041961, both of which are incorporated herein by reference in their entirety.

All of the above are fully within the scope of the present disclosure, and are considered to form the basis for alternative embodiments in which one or more combinations of the above described features are applied, without limitation to the specific combinations disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptions fall within the scope of the present disclosure.

The invention claimed is:

1. An embolization device for promoting clot formation in a bodily lumen and having a contracted delivery configuration and an expanded deployed configuration, the embolization device comprising:
   a stem comprising a tube having a tube wall and a central lumen; and
   a plurality of flexible bristles extending radially outwardly from the tube, wherein at least one of the plurality of flexible bristles penetrates through the tube wall and the at least one of the plurality of flexible bristles has a clamped portion within the central lumen,
   wherein the tube is formed from a shrinkable material.

2. The embolization device of claim 1, wherein the shrinkable material is a heat or chemically shrinkable material.

3. The embolization device of claim 1, wherein the tube is shrunk and wherein the plurality of flexible bristles are each clamped within the central lumen.

4. The embolization device of claim 3, wherein the tube is shrunk in a radial direction of the tube.

5. The embolization device of claim 1, wherein the tube is mechanically compressed in a radial direction and wherein the plurality of flexible bristles are each clamped within the central lumen.

6. A method of manufacturing an embolization device for promoting clot formation in a lumen having a contracted delivery configuration and an expanded deployed configuration, the method comprising:
   providing a stem comprising a tube having a tube wall; and
   providing a plurality of flexible bristles such that they extend radially outwardly from the tube,
   wherein at least one of the plurality of flexible bristles penetrates through the tube wall; further comprising shrinking or mechanically compressing the tube such that a portion of the at least one of the plurality of flexible bristles is clamped between two opposing sides of the tube wall.

7. The method of claim 6, wherein the tube is shrunk or compressed in a radial direction of the tube.

8. The method of claim 6, wherein the tube is mechanically compressed in a radial direction such that a portion of the at least one of the plurality of flexible bristles is clamped between two opposing sides of the tube wall, and, optionally, wherein the tube is mechanically compressed by crimping.

\* \* \* \* \*